US012600984B2

(12) United States Patent     (10) Patent No.:   US 12,600,984 B2

Williams                       (45) Date of Patent:     Apr. 14, 2026

(54) VIRAL AND NON-VIRAL NANOPLASMID VECTORS WITH IMPROVED PRODUCTION

(71) Applicant: Aldevron, L.L.C., South Fargo, ND (US)

(72) Inventor: James A. Williams, Lincoln, NE (US)

(73) Assignee: Aldevron, L.L.C., South Fargo, ND (US)

( * ) Notice: Subject to any disclaimer, the term of this patent is extended or adjusted under 35 U.S.C. 154(b) by 1111 days.

(21) Appl. No.: 17/026,101

(22) Filed: Sep. 18, 2020

(65) Prior Publication Data

US 2021/0010021 A1     Jan. 14, 2021

Related U.S. Application Data

(63) Continuation of application No. PCT/US2019/023209, filed on Mar. 20, 2019.

(60) Provisional application No. 62/645,892, filed on Mar. 21, 2018.

(51) Int. Cl.

| | |
|---|---|
| *C12N 15/85* | (2006.01) |
| *C12N 15/70* | (2006.01) |
| *C12N 15/86* | (2006.01) |

(52) U.S. Cl.

CPC ............. *C12N 15/85* (2013.01); *C12N 15/70* (2013.01); *C12N 15/86* (2013.01); *C12N 2740/15043* (2013.01); *C12N 2740/15052* (2013.01); *C12N 2750/14143* (2013.01); *C12N 2750/14152* (2013.01); *C12N 2800/90* (2013.01); *C12N 2820/55* (2013.01)

(58) Field of Classification Search

CPC ........ C12N 15/85; C12N 15/70; C12N 15/86; C12N 2740/15043; C12N 2740/15052; C12N 2750/14143; C12N 2750/14152; C12N 2800/90; C12N 2820/55; C12N 2800/101; C12N 2800/24

See application file for complete search history.

(56) References Cited

U.S. PATENT DOCUMENTS

| | | | |
|---|---|---|---|
| 5,922,583 | A | 7/1999 | Morsey |
| 6,709,844 | B1 | 3/2004 | Levy |
| 6,977,174 | B2 | 12/2005 | Crouzet et al. |
| 7,244,609 | B2 | 7/2007 | Drocourt et al. |
| 7,611,883 | B2 | 11/2009 | Cranenburgh |
| 7,943,377 | B2 | 5/2011 | Carnes et al. |
| 9,012,226 | B2 | 4/2015 | Williams |
| 9,017,966 | B2 | 4/2015 | Williams et al. |
| 9,018,012 | B2 | 4/2015 | Williams |
| 9,506,082 | B2 | 11/2016 | Williams |
| 9,550,998 | B2 | 1/2017 | Williams |
| 9,950,081 | B2 * | 4/2018 | Williams ............. A61K 39/145 |
| 2003/0180949 | A1 | 9/2003 | Levy |

| | | | |
|---|---|---|---|
| 2004/0072326 | A1 * | 4/2004 | Cayota Guzicovsky ................... C07K 14/524 435/252.3 |
| 2006/0063232 | A1 | 3/2006 | Grabherr et al. |
| 2009/0298909 | A1 | 12/2009 | Pachuk |
| 2010/0184158 | A1 | 7/2010 | Williams |
| 2013/0344604 | A1 | 12/2013 | Aebischer-Gumy |
| 2015/0191735 | A1 * | 7/2015 | Williams ............... C12N 15/85 435/69.3 |
| 2015/0275221 | A1 | 10/2015 | Williams |
| 2016/0008488 | A1 * | 1/2016 | Williams ............. C12N 15/117 424/234.1 |

FOREIGN PATENT DOCUMENTS

| | | |
|---|---|---|
| CA | 2794446 | 10/2002 |
| CN | 1665930 | 9/2005 |
| CN | 101932708 | 12/2010 |
| EP | 13100166 A1 | 5/2003 |
| EP | 1642970 A1 | 4/2006 |
| EP | 1921140 A1 | 5/2008 |
| JP | H04-197185 A | 7/1992 |
| JP | H11-502705 A | 3/1999 |
| JP | 2016-521553 A | 7/2016 |
| JP | 2021-518150 A | 3/2019 |

(Continued)

OTHER PUBLICATIONS

Carnes et al. ECI Digital Archives, Vaccine Technology VI, Jun. 12, 2016 (Year: 2016).*

Lu et al. (Human Gene Therapy, 2016, 28(1), p. 125-134, Supplementary Figure S2) (Year: 2016).*

(Continued)

*Primary Examiner* — Jeremy C Flinders

*Assistant Examiner* — Masudur Rahman

(74) *Attorney, Agent, or Firm* — FBT Gibbons LLP

(57) ABSTRACT

A method for improving the replication of a covalently closed circular plasmid is provided. The method includes providing a covalently closed circular plasmid having a Pol I-dependent origin of replication, and an insert including a structured DNA sequence selected from inverted repeat sequences, direct repeat sequences, homopolymeric repeat sequences, eukaryotic origins of replication or eukaryotic promoter enhancer sequences, wherein the structured DNA sequence is located at a distance of less than 1000 bp from the Pol I-dependent origin of replication in the direction of replication. The method also includes modifying the covalently closed circular recombinant molecule such that the Pol I-dependent origin of replication is replaced with a Pol III-dependent origin of replication, whereby the resultant Pol III-dependent origin of replication covalently closed circular plasmid has improved replication. An antibiotic marker free covalently closed circular recombinant DNA molecule is also provided.

31 Claims, 5 Drawing Sheets

Specification includes a Sequence Listing.

(56) References Cited

FOREIGN PATENT DOCUMENTS

| WO | 96/30531 A | 10/1996 | |
| WO | WO-9630531 A1 * | 10/1996 | ........... C07K 14/505 |
| WO | 2002/013602 A | 2/2002 | |
| WO | WO-0213602 A1 * | 2/2002 | ......... A01K 67/0275 |
| WO | 2004033664 A2 | 12/2004 | |
| WO | 2005/003342 A | 1/2005 | |
| WO | WO-2005003342 A1 * | 1/2005 | ......... A01K 67/0275 |
| WO | 2007/004642 A | 1/2007 | |
| WO | WO-2007004642 A1 * | 1/2007 | ........... C12N 15/102 |
| WO | 2008153733 A2 | 12/2008 | |
| WO | 2014035457 A1 | 3/2014 | |
| WO | 2014077863 A1 | 5/2014 | |
| WO | 2014077866 A1 | 5/2014 | |
| WO | 2014/195920 A2 | 12/2014 | |
| WO | 2017025447 A1 | 2/2017 | |
| WO | 2017066579 A1 | 4/2017 | |
| WO | 2020132396 A1 | 6/2020 | |

OTHER PUBLICATIONS

Carnes, A., Tiwari, N., Beilowitz, J., Sampson, C., Peterson, D. and Williams, J., 2016. Production of a Nanoplasmid™ with a large gene insert using the HyperGRO™ fermentation process. ECI Digital Archives, Vaccine Technology VI, Jun. 12, 2016 (Year: 2016).*

Williams, S.L., Casas-Delucchi, C.S., Raguseo, F., Guneri, D., Li, Y., Minamino, M., Fletcher, E.E., Yeeles, J.T., Keyser, U.F., Waller, Z.A. and Di Antonio, M., 2023. Replication-induced DNA secondary structures drive fork uncoupling and breakage. The EMBO journal, 42(22), p. e114334. (Year: 2023).*

Office Action mailed Dec. 29, 2023 in Chinese Patent Application No. 201980034026.9.

Office Action mailed Jan. 9, 2024 in Japanese Patent Application No. 2020-551263.

Official Action issued on Mar. 14, 2023, in Japanese Patent Application No. 2020-551263.

Carnes A et al, Production of a Nanoplasmid with a large gene insert using the HyperGRO fermentation process, Engineering Conferences International ECI Digital Archives, Vaccine Technology VI2016.

European Search Report issued on Jan. 25, 2023, in European Patent Application No. 22194460.6.

Office Action (and English translation) dated Aug. 8, 2023 for Japanese Patent Application No. 2020-551263.

Abhyankar et al.; Reconstitution of R6K Dna Replication in Vitro Using 22 Purified Proteins; 2003 J Biol Chem 278:45476-45484.

Abhyankar et al.; Biochemical Investigations of Control of Replication Initiation of Plasmid R6K; 2004 J Biol Chem 279:6711-6719.

Allen et al.; Roles of DNA polymerase I in leading and lagging-strand replication defined by a high-resolution mutation footprint of ColE1 plasmid replication; 2011 Nucleic Acids Research 39:7020-33.

Carnes et al.; Critical design criteria for minimal antibiotic-free plasmid vectors necessary to combine robust RNA Pol II and Pol III-mediated eukaryotic expression with high bacterial production yields; J Gene Medicine; Oct. 2010; 12(10):818-831.

Carnes A.E.; Fermentation Design for the Manufacture of Therapeutic Plasmid DNA; 2005 BioProcess Intl 3:36-44.

Chadeuf et al.; Evidence for Encapsidation of Prokaryotic Sequences during Recombinant Adeno-Associated Virus Production and Their in Vivo Persistence after Vector Delivery; 2005 Molecular Therapy, vol. 12, No. 4:744-753.

Chenna et al.; Evidence for Encapsidation of Prokaryotic Sequences during Recombinant Adeno-Associated Virus Production and Their in Vivo Persistence after Vector Delivery; 2003 Nucleic Acids Res., vol. 31, No. 13:3497-3500.

Chen ZY, He CY, Meuse L, Kay MA; Silencing of episomal transgene expression by plasmid bacterial DNA elements in vivo; 2004 Gene Ther 11:856-864.

Del Solar et al.; Replication and Control of Circular Bacterial Plasmids; 1998 Microbiol. Mol. Biol. Rev vol. 62, No. 2:434-464.

Elango et al.; Optimized transfection of mRNA transcribed from a d(A/T)100 tail-containing vector; Biochemical and Biophysical Research Communications 330(2005):958-966.

Franch T, and Gerdes K.; U-turns and regulatory RNAs; 2000. Current Opin Microbiol 3:159-164.

Godiska, Ronald & Patterson, Melodee & Schoenfeld, Tom & Mead, David. (2005). Mini Review Beyond pUC: Vectors for Cloning Unstable Dna. Dna Sequencing: Optimizing the Process and Analysis; pp. 55-75.

Hebel HL, Cai Y, Davies LA, Hyde SC, Pringle IA, Gill DR; Challenges in the Process Development of a Novel Zero CpG CFTR Plasmid for Human Clinical Use; 2008 Molecular Therapy; vol. 16, Supp. 1: S110.

Holstein et al.; Efficient Non-viral Gene Delivery into Human Hematopoietic Stem Cells by Minicircle Sleeping Beauty Transposon Vectors; (2018) Molecular Therapy epub Jan. 17, 2018.

Karbownickez et al.; Doggybone DNA: an advanced platform for AAV production; 2017. Cell and Gene Therapy Insights 731-738.

Kay, Mark; et al.; A Robust System for Production of Minicircle DNA Vectors; Dec. 2010 Nat Biotechnol 28(12):1287-1289.

Krasilnikova, et al.; Transcription through a simple DNA repeat blocks replication elongation; EMBO Journal; v. 17; No. 17; pp. 5095-5102 (1998).

Lu J., et al.; The Extragenic Spacer Length Between the 5' and 3' Ends of the Transgene Expression Cassette Affects Transgene Silencing from Plasmid-based Vectors; 2012 Mol Ther. vol. 20, No. 11:2111-2119.

Lu, J., et al.: "A 5' Noncoding Exon Containing Engineered Intron Enhances Trangene Expression from Recombinant AAV Vectors in Vivo", Human Gene Therapy, vol. 28, No. 1, Jan. 1, 2017 (Jan. 1, 2017), pp. 125-134.

Luke et al.; Vector Insert-Targeted Integrative Antisense Expression System for Plasmid Stabilization; 2011 Mol Biotechnol 47:43.

Marie et al.; pFARs, Plasmids free of antibiotic resistance markers, display high-level transgene expression in muscle, skin and tumour cells; (2010) J. Gene Medicine 12:323-332.

Marino MP, Luce MJ, Reiser J.; Small- to Large-Scale Production of Lentivirus Vectors; 2003, Methods Mol Biol 229:43-55.

Mirkin and Mirkin; Replication Fork Stalling at Natural Impediments; 2007 Microbiology and Molecular Biology Reviews 71:13-35.

Monjezi, et al.; Enhanced CAR T-cell engineering using non-viral Sleeping Beauty transposition from minicircle vectors; (2017) Leukemia 31:186-194.

Mutalik et al.; Rationally designed families of orthogonal RNA regulators of translation; 2012 Nat Chem Biol 8:447-454.

Na D., et al.; Metabolic engineering of Escherichia coli using synthetic small regulatory NRAs; 2013 Nat Biotechnol 31:170-174.

Pastor, M., et al.; The Antibiotic-free pFAR4 Vector Paired with the Sleeping Beauty Transposon System Mediates Efficient Transgene Delivery in Human Cells; 2018 Molecular Therapy 11:57-67.

Quiviger, M., et al.; High and prolonged sulfamidase secretion by the liverof MPS-IIIA mice following hydrodynamic tail vein delivery of antibiotic-free pFAR4 plasmid vector; 2014 Gene Therapy 21:1001-1007.

Ribeiro et al., Plasmid DNA Size Does Affect Nonviral Gene Delivery Efficiency in Stem Cells; 2011 Cell Reprogram vol. 14, No. 2:130.

Schnodt et al., DNA Minicircle Technology Improves Purity of Adeno-associated Viral Vector Preparations; 2016 Mol Ther - Nucleic Acids 5 e355.

Sharma et al.; Efficient Sleeping Beauty DNA Transposition From DNA Minicircles; 2013 Molecular Therapy Nucleic Acids 2:e74.

Soubrier, et al.; pCOR: a new design of plasmid vectors for nonviral gene therapy; 1999 Gene Therapy 6:1482-1488.

Suzuki M., et al.; Plasmid DNA Sequences Present in Conventional Herpes Simplex Virus Amplicon Vectors Cause Rapid Transgene Silencing by Forming Inactive Chromatin; 2006. J Virol 80(7):3293-3300.

(56)          References Cited

OTHER PUBLICATIONS

Tipanee, J., et al.; Preclinical and clinical advances in transposon-based gene therapy; 2017 Bioscience reports, 37(6), BSR20160614. https://doi.org/10.1042/BSR20160614.

Wagner, E., et al.; Antisense RNAs in Bacteria and Their Genetic Elements; 2002 Adv Genet 46:361-398.

Wang et al., In Vivo Electroporation of Minicircle DNA as a Novel Method of Vaccine Delivery To Enhance HIV-1- Specific Immune Responses; 2014 J Virology 88:1924-34.

Williams, J.A., et al.; Plasmid DNA Vaccine Vector Design: Impact on Efficacy, Safety, and Upstream Production; Biotechnology Advances, Elsevier Publishing, Barking, GB, vol. 27, No. 4, Jul. 1, 2009 (Jul. 1, 2009).

Wilson, I. W., et al.; Importance of Structural Differences between Complementary RNA Molecules to Control of Replication of an IncB Plasmid; 1997 J Bacteriol 179(3):742-53.

Wu, F., et al.; A DNA Segment Conferring Stable Maintenance on R6K y-Origin Core Replicons; 1995 J Bacteriol. 177(22): 6338-6345.

International Search Report and Written Opinion of related application PCT/US19/23209, dated May 22, 2019.

Office Action mailed Nov. 6, 2024 in Chinese Patent Application No. 201980034026.9.

Office Action mailed Nov. 25, 2024 in Canadian Patent Application No. 3,093,346.

Office Action mailed Oct. 30, 2024 in Korean Patent Application No. 10-2020-7030139.

Lu, et al., "Multi-origin usage for chromosome replication of suppressive integration strain of dnaA46 mutant of *Escherichia coli* integrated with R6K," Yi Chuan Xue Bao. 1992;19(1):86-92. Chinese. PMID: 1599714.

Search Report mailed Dec. 29, 2023 in Chinese Patent Application No. 201980034026.9.

* cited by examiner

R6K origin annotations with SEQ ID regions
390 bp

SEQ ID 5 RNA-OUT selectable marker
139 bp

SEQ ID 8 RNA-OUT (14 CpG)
466 bp

SEQ ID 9 R6K-RNA-OUT (3 CpG)
439 bp

FIG. 1E

SEQ ID NO: 1 R6K origin (6 Iteron)
281 bp

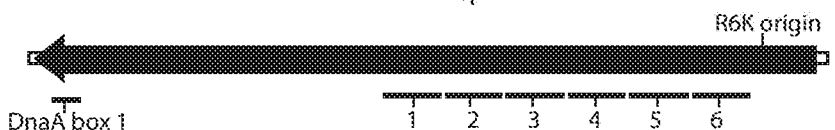

DnaA box 1          1   2   3   4   5   6          R6K origin

Iteron 1: AAACATGAGAGCTTAGTACGTG SEQ ID NO: 19

Iteron 2: AAACATGAGAGCTTAGTACGTT SEQ ID NO: 20

Iteron 3: AGCCATGAGAGCTTAGTACGTT SEQ ID NO: 21

Iteron 4: AGCCATGAGGGTTTAGTTCGTT SEQ ID NO: 22

Iteron 5: AAACATGAGAGCTTAGTACGTT SEQ ID NO: 20

Iteron 6: AAACATGAGAGCTTAGTACGTA SEQ ID NO: 23

FIG. 1F

SEQ ID NO: 18 R6K origin (7 Iteron)
303 bp

R6K origin (interon duplication)

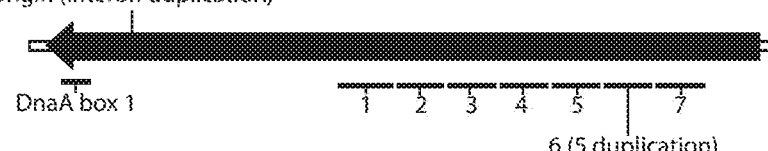

DnaA box 1          1   2   3   4   5       7
                              6 (5 duplication)

Iteron 1: AAACATGAGAGCTTAGTACGTG SEQ ID NO: 19

Iteron 2: AAACATGAGAGCTTAGTACGTT SEQ ID NO: 20

Iteron 3: AGCCATGAGAGCTTAGTACGTT SEQ ID NO: 21

Iteron 4: AGCCATGAGGGTTTAGTTCGTT SEQ ID NO: 22

Iteron 5: AAACATGAGAGCTTAGTACGTT SEQ ID NO: 20

Iteron 6: AAACATGAGAGCTTAGTACGTT SEQ ID NO: 20

Iteron 7: AAACATGAGAGCTTAGTACGTA SEQ ID NO: 23

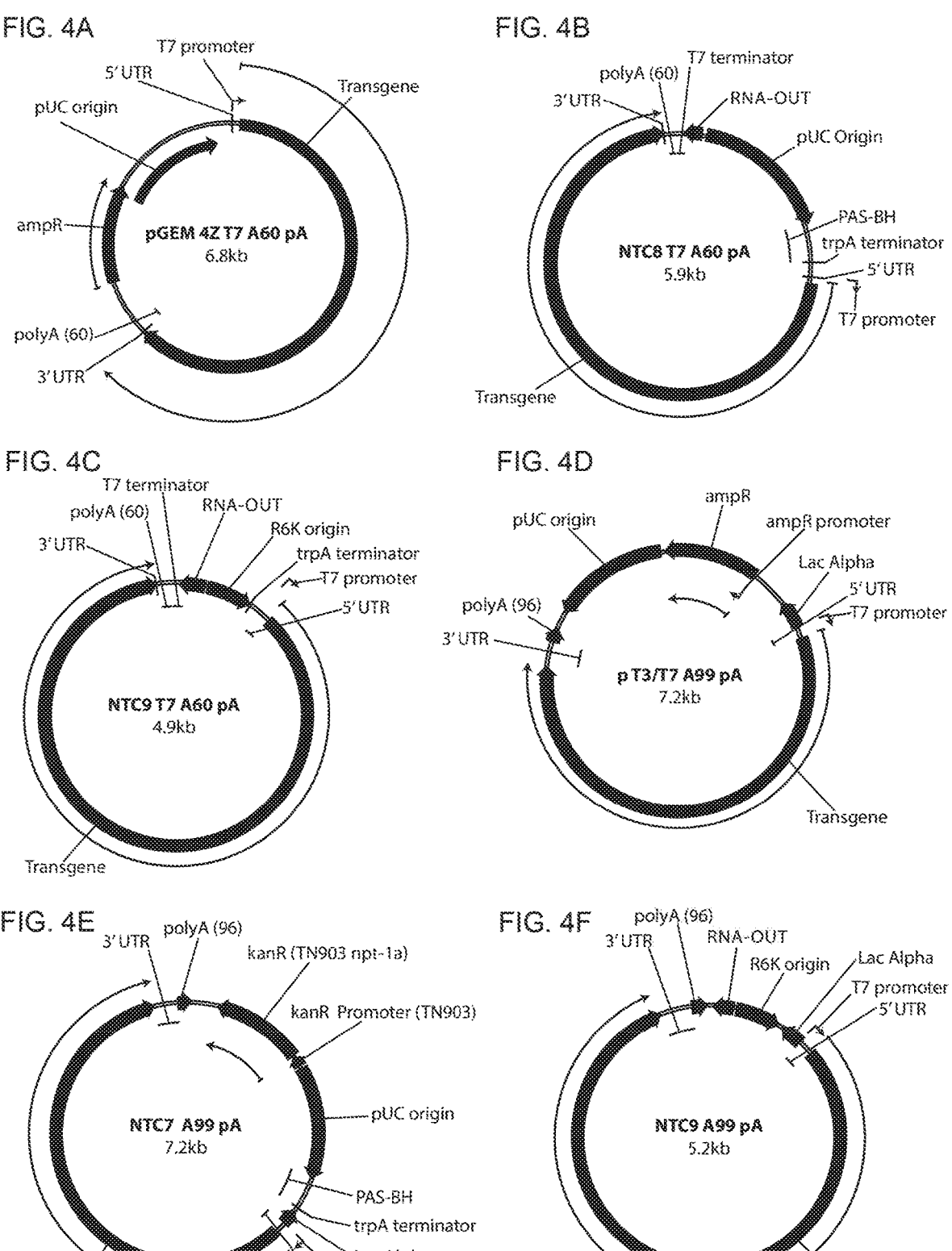

FIG. 4A pGEM 4Z T7 A60 pA
6.8kb

T7 promoter
5′UTR
pUC origin
Transgene
ampR
polyA (60)
3′UTR

FIG. 4B

NTC8 T7 A60 pA
5.9kb

T7 terminator
polyA (60)
3′UTR
RNA-OUT
pUC Origin
PAS-BH
trpA terminator
5′UTR
T7 promoter
Transgene

FIG. 4C

NTC9 T7 A60 pA
4.9kb

T7 terminator
polyA (60)
RNA-OUT
3′UTR
R6K origin
trpA terminator
T7 promoter
5′UTR
Transgene

FIG. 4D pT3/T7 A99 pA
7.2kb pUC origin
ampR
ampR promoter
Lac Alpha
5′UTR
polyA (96)
3′UTR
T7 promoter
Transgene

FIG. 4E

NTC7 A99 pA
7.2kb

3′UTR
polyA (96)
kanR (TN903 npt-1a)
kanR Promoter (TN903)
pUC origin
PAS-BH
trpA terminator
Lac Alpha
T7 promoter
5′UTR
Transgene

FIG. 4F

NTC9 A99 pA
5.2kb polyA (96)
3′UTR
RNA-OUT
R6K origin
Lac Alpha
T7 promoter
5′UTR
Transgene

VIRAL AND NON-VIRAL NANOPLASMID VECTORS WITH IMPROVED PRODUCTION

CROSS REFERENCE TO RELATED APPLICATIONS

This application is a continuation of international Patent Application No. PCT/US19/23209, filed Mar. 20, 2019, which claims priority to U.S. Provisional Patent Application Ser. No. 62/645,892, filed Mar. 21, 2018, the disclosures of which are incorporated herein by reference.

STATEMENT REGARDING FEDERALLY SPONSORED RESEARCH OR DEVELOPMENT

Not applicable.

FIELD OF THE INVENTION

The present invention relates to recombinant DNA molecules. i.e., vectors, useful for viral and non-viral gene therapy, viral and non-viral cell therapy, and more particularly, for improving viral and non-viral vector manufacturing yield and quality, reducing transfection associated toxicity, improving transposition from non-viral transposon vectors, improving packaging titers from viral vectors, improving expression of viral and non-viral vector encoded genes, and for eliminating viral vector and non-viral vector mediated antibiotic selection marker gene transfer.

Such recombinant DNA molecules are useful in biotechnology, ex vivo gene therapy, transgenic organisms, gene therapy, therapeutic vaccination, agriculture and DNA vaccines.

BACKGROUND OF THE INVENTION

E. coli plasmids have long been an important source of recombinant DNA molecules used by researchers and by industry. Today, plasmid DNA is becoming increasingly important as the next generation of biotechnology products (e.g. gene medicines and DNA vaccines) make their way into clinical trials, and eventually into the pharmaceutical marketplace. Plasmid DNA vaccines may find application as preventive vaccines for viral, bacterial, or parasitic diseases; immunizing agents for the preparation of hyper immune globulin products; therapeutic vaccines for infectious diseases; or as cancer vaccines. Plasmids are also utilized in gene therapy or gene replacement applications, wherein the desired gene product is expressed from the plasmid after administration to a patient. Plasmids are also utilized in non-viral transposon vectors for gene therapy or gene replacement applications, wherein the desired gene product is expressed from the genome after transposition from the plasmid and genome integration. Plasmids are also utilized in viral vectors for gene therapy or gene replacement applications, wherein the desired gene product is packaged in a transducing virus particle after transfection of a production cell line, and is then expressed from the virus in a target cell after viral transduction.

Non-viral and viral vector plasmids typically contain a pMB1, ColE1 or pBR322 derived replication origin. Common high copy number derivatives have mutations affecting copy number regulation, such as ROP (Repressor of primer gene) deletion, with a second site mutation that increases copy number (e.g. pMB1 pUC G to A point mutation, or ColE1 pMM1). Higher temperature (42° C.) can be employed to induce selective plasmid amplification with pUC and pMM1 replication origins.

Carnes, A E and Williams, J A, 2011 U.S. Pat. No. 7,943,377 describe methods for fed-batch fermentation, in which plasmid-containing E. coli cells were grown at a reduced temperature during part of the fed-batch phase, during which growth rate was restricted, followed by a temperature up-shift and continued growth at elevated temperature in order to accumulate plasmid; the temperature shift at restricted growth rate improved plasmid yield and purity. Other fermentation processes for plasmid production are described in Carnes A. E. 2005 BioProcess Intl 3:36-44, which is incorporated herein by reference in its entirety.

The art teaches that one of the limitations of application of plasmid therapies and plasmid vaccines is regulatory agency (e.g. Food and Drug Administration, European Medicines Agency) safety concerns regarding: 1) plasmid transfer and replication in endogenous bacterial flora, or 2) plasmid encoded selection marker expression in human cells, or endogenous bacterial flora. Additionally, regulatory agency guidance's recommend removal of all non-essential sequences in a vector. Plasmids containing a pMB1, ColE1 or pBR322 derived replication origin can replicate promiscuously in E. coli hosts. This presents a safety concern that a plasmid therapeutic gene or antigen will be transferred to, and replicated within, a patient's endogenous flora. Ideally, a therapeutic or vaccine plasmid would be replication incompetent in endogenous E. coli strains. This requires replacement of the pMB1, ColE1 or pBR322 derived replication origin with a conditional replication origin that requires a specialized cell line for propagation. As well, regulatory agencies, such as the EMEA and FDA, are concerned with utilization of antibiotic resistance or alternative protein markers in gene therapy and gene vaccine vectors, due to concerns that the gene (antibiotic resistance marker or protein marker) may be expressed in a patient's cells. Ideally, plasmid therapies and plasmid vaccines would: 1) be replication incompetent in endogenous E. coli strains, 2) not encode a protein-based selection marker and 3) be minimalized to eliminate all non-essential sequences.

The art further teaches that one of the limitations of application of plasmid vectors is that transgene expression duration from plasmid vectors is reduced due to promoter inactivation mediated by the bacterial region (i.e. the region encoding the bacterial replication origin and selectable marker) of the vector (Chen Z Y, He C Y, Meuse L, Kay M A. 2004. Gene Ther 11:856-864; Suzuki M, Kasai K, Saeki Y. 2006. J Virol 80:3293-3300). This results in short duration transgene expression. A strategy to improve transgene expression duration is to remove the bacterial region of the plasmid. For example, minicircle vectors have been developed which do not contain a bacterial region. Removal of the bacterial region in minicircle vectors improved transgene expression duration (Chen et al., Supra, 2004). In minicircle vectors, the eukaryotic region polyadenylation signal is covalently linked to the eukaryotic region promoter through a short spacer typically less than 200 bp comprised of the recombined attachment sites. This linkage (spacer region) can tolerate a much longer spacer sequence since while long spacers ≥1 kb in length resulted in transgene expression silencing in vivo, shorter spacers ≤500 bp exhibited similar transgene expression patterns to conventional minicircle DNA vectors (Lu J, Zhang F, Xu S, Fire A Z, Kay M A. 2012. Mol Ther. 20:2111-9).

Williams, 2014. DNA plasmids with improved expression. World Patent Application WO2014035457 disclose minimalized Nanoplasmid™ vectors utilize RNA-OUT antibiotic-free selection and replace the large 1000 bp pUC replication origin with a novel. 300 bp, R6K origin. Reduction of the spacer region linking the 5' and 3' ends of the transgene expression cassette to <500 bp with R6K origin-RNA-OUT backbones improved expression duration to that of conventional minicircle DNA vectors as expected from the teachings of Lu et al., *Supra,* 2012.

The 1.1 kb pFAR4 vector pUC-origin tRNA antibiotic free selection spacer has improved expression duration compared to a 2.2 kb pUC origin-kanR antibiotic selection marker spacer region (Quiviger, M, Arfi A, Mansard D, Delacotte L, Pastor M, Scherman D, Marie C. 2014. *Gene Therapy* 21:1001-1007). This teaches that improved expression duration can be obtained with some bacterial regions up to 1.1 kb.

Expression level improvement compared to plasmid vectors is also observed with some spacer regions ≤1.1 kb. For example, pVAX1 derivatives with the 2 kb bacterial backbone reduced to 1.2, 1.1 or 0.7 kb show ≥2-fold improved expression compared to the parent pVAX1 vector (Table 1). NTC8685 derivatives with the 1.5 kb bacterial backbone reduced to 0.9 kb, 466 bp or 281 bp (Nanoplasmid™ vectors) show ≥2-fold improved expression compared to the parent NTC8685 vector (Table 2).

This teaches that improved expression level can be obtained with short bacterial regions up to 1.2 kb.

TABLE 1

| pVAX1 mammalian expression vector spacer region (SR) derivatives expression level | | | | | |
|---|---|---|---|---|---|
| pVAX1 Vector derivatives | Bacterial Backbone (bp) | Selection Marker | Selection | In Vitro Expression | In vivo Expression |
| pVAX1 | 2 kb | KanR | Kan | 1X (baseline) | 1X (baseline) |
| pVAX1-A2[a] | 1.2 kb | RNA-OUT | Sucrose | 4x | ND |
| pVAX1/MINI[b] | 0.7 kb | RNAI (pUC origin) | murA translation | 2x | ND |
| pFAR4[c] | 1.1 kb | tRNA (amber) | thyA amber mutation suppression | ND | >5x ID EP |
| Minicircle[d] | 50 bp | NA, Minicircle | NA, Minicircle | 1.4-1.6x (equimolar dose) | 1.3x IM (equimolar dose) |

[a]Carnes et al., (2010) *J. Gene Medicine* 12: 818-31
[b]Ribeiro et al., (2011) *Cell Reprogram* 14: 130
[c]Marie et al., (2010) *J. Gene Medicine* 12: 323-32
[d]Wang et al., (2014) *J Virology* 88: 1924-34

TABLE 2

| NTC8685 mammalian expression vector spacer region (SR) derivatives expression level | | | | | |
|---|---|---|---|---|---|
| NTC8685 Vector derivatives[a] | Replication origin | Bacterial backbone (bp) | Selection Marker | In vitro Expression (A549) | In vivo Expression (ID + EP) |
| NTC8685 | pUC origin | 1.5 kb | RNA-OUT | 1X (baseline) | 1X (baseline) |
| NTC8385-Min | Minimalized pUC origin | 0.9 kb | RNA-OUT | 2.1x | 1.4-1.9x |
| NTC9385R Nanoplasmid ™ | R6K origin | 466 bp | RNA-OUT | 2.5x | 5.3-6.3x |
| NTC9385C Nanoplasmid ™ | ColE2 origin | 281 bp | RNA-OUT | 1.1x | 2.7-3.1x |

[a]Williams, *Supra,* 2014

Various investigators have identified that minicircle vectors are superior to plasmid vectors for production of AAV vectors (improved transducing unit titers—Table 3) and transposon vectors (increased transposition—Table 3). The improved performance due to improved expression duration with short backbone minicircle vectors should also be observed with short bacterial backbone plasmid vectors up to 1.1 kb,

TABLE 3

| Minicircle applications with various viral and non-viral vector platforms | | | | |
|---|---|---|---|---|
| Vector platform | pUC Plasmid (>1.5 kb pUC origin-antibiotic marker spacer region) | Minicircle (MC) retrofit (<400 bp spacer region) | Result-performance | Result-antibiotic marker gene transfer |
| self-complementary (sc) AAV | pAAV-scGFP | MC.AAVscGFP | Up to 30-fold improved Transducing units[a] | Plasmid backbone antibiotic resistance marker packaged in up to 26.1% viral particles[a] |

TABLE 3-continued

| | | | | |
|---|---|---|---|---|
| Vector platform | pUC Plasmid (>1.5 kb pUC origin-antibiotic marker spacer region) | Minicircle (MC) retrofit (<400 bp spacer region) | Result-performance | Result-antibiotic marker gene transfer |
| single-stranded (ss) AAV | AAV2-ssGFP | MC.AAV-ssGFP | Up to 3-fold improved Transducing units[a] | potential for genome integration in transduced cells Plasmid backbone antibiotic resistance marker packaged in up to 2.9%[a] or 3%[b] of viral particles potential for genome integration in transduced cells |
| Sleeping Beauty Transposon | SB puroR reporter plasmid | SB puroR reporter MC | 2-fold increased transposition rate into established cell lines[c] | Plasmid backbone antibiotic resistance potential for genome integration in T-cells |
| | SB CD19-CAR | MC: SB CD19 CAR | 4-fold increased yield of CD19-CAR T-cells; reduced transfection associated toxicity[d] | |
| | SB | MC: SB (218 bp MC Backbone) | 6-7-fold increased transposition into Human Hematopoietic Stem cells; reduced transfection associated toxicity[e] | |

[a]Schnödt et al., (2016) *Mol Ther - Nucleic Acids* 5 e355. This citation, along with Chadeuf et al., (2005) *Molecular Therapy* 12: 744-53 and Gray, 2017. WO2017066579 also reports that AAV helper plasmid antibiotic resistance markers are packaged into viral particles, demonstrating need to remove antibiotic markers from AAV helper plasmids as well as the AAV vector. Interestingly, no improvement in viral titer compared to plasmid is observed with linear Doggybone ™ DNA single-stranded (ss) AAV vector retrofits (Karbownickez et al., 2017. *Cell and Gene Therapy Insights* 731-8). This suggests that short backbone minicircle vector improvement compared to >1.5 kb pUC-antibiotic marker plasmid backbone vectors require a short backbone circular vector rather than a linear vector such as Doggybone ™ vectors.
[b]Gray, *Supra*, 2017 describes adding a large spacer region to move selection marker away from ITRs. Resultant vector, pAAV CMV GFP is 11 kb compared to 5-6 kb for standard plasmid AAV vector so will have reduced transducing units compared to parental
[c]Sharma et al., (2013) *Molecular Therapy Nucleic Acids* 2: e74
[d]Nucleofection transfection: Monjezi et al., (2017) *Leukemia* 31: 186-94
[e]Nucleofection transfection: Holstein et al., (2018) *Molecular Therapy* epub Jan. 17, 2018

Indeed 2-fold improved sleeping beauty transposition into human cells was reported with the 1.1 kb bacterial backbone pFAR4 SB transposon vector/SB100x transposase vector combination compared to a 2.8 kb bacterial backbone pT2 plasmid SB transposon vector/SB100x transposase vector combination (Pastor, M, Johnen S, Harmening N, Quiviger M, Pailloux J, Kropp, M, Walter P, Ivies Z, Izsvak Z, Thumann G, Scherman D. 2018 *Molecular Therapy* 11: 57-67).

However, viral vectors such as AAV, Lentiviral and Retroviral vectors, and transposon vectors contained structured DNA sequences at their termini. For example, Sleeping Beauty transposon vectors contain flanking IR/DR sequences, AAV vectors contain flanking ITRs, and Lentiviral and Retroviral vectors contain flanking LTRs.

The close proximity of the pUC origin to a structured DNA sequence results in aberrant replication termination, resulting in replication intermediates which unacceptably reduce plasmid quality (Levy J. 2004, U.S. Pat. No. 6,709, 844). Levy teaches that replication intermediates form when any high copy replication origin is <1 kb from a structured DNA sequence such as an enhancer, LTR or IRES, but not when the high copy replication origin is >1.5 kb away. Since the pUC origin itself is 1 kb, there is no configuration to make a <1.1 kb bacterial region AAV, Lentiviral, Retroviral or transposon vector containing the pUC origin which is not predicted to produce replication intermediates.

Lu J, Williams J A, Luke J, Zhang F, Chu K, and Kay M A. 2017. *Human Gene Therapy* 28:125-34 disclose antibiotic free Mini-Intronic Plasmid (MIP) AAV vectors and suggest that MIP intron AAV vectors could have the vector backbone removed to create a short backbone AAV vector. Attempts to create a minicircle like 6 or 10 bp spacer region in Mini-Intronic Plasmid AAV vectors were toxic (see Table 7, footnote e) presumably due to creation of a long palindrome by such close juxtaposition of the AAV ITRs. While MIP vectors with longer spacer regions <1 kb can be made, a drawback of the MIP intron strategy is that it requires cloning of a replication and selection encoding intron into the eukaryotic region, which is not possible or desired with many vectors.

A drawback of the minicircle strategy to create short bacterial region AAV, Lentiviral, Retroviral or transposon vectors, is that methods to manufacture minicircle vectors are expensive and not easily scalable. For minicircle vectors, *E. coli*-based manufacturing systems have been developed in which, after plasmid production, the bacterial region and the eukaryotic region are separated and circularized into a minicircle (eukaryotic region) and a bacterial region circle via the action of phage recombinases on recognition sequences in the plasmid. In some methods, a restriction enzyme is then utilized to digest the bacterial region circle at a unique site to eliminate this difficult to remove contaminant. These production procedures are very inefficient. For example, optimal manufacture of minicircle vectors yields only 5 mg of minicircle per liter culture (Kay M A, He C Y, Chen Z Y. 2010. *Nat Biotechnol* 28:1287-1289).

Methods for high yield manufacture of pFAR vectors have not been reported; this system utilizes a plasmid borne suppressor tRNA gene to complement a TAG amber nonsense mutation of the thyA gene to complement thymidine auxotrophy and allow cell growth on minimal media (Marie et al., *Supra*, 2010).

A solution is needed to develop AAV, Lentiviral, Retroviral or transposon vector that contain short spacer regions preferably less than 1000 bp that can be efficiently manufactured without replication intermediates or poor production. These vectors should not encode a protein-based selection marker and should be minimalized to eliminate all non-essential sequences.

SUMMARY OF THE INVENTION

The present invention relates to vectors useful for viral and non-viral gene therapy, viral and non-viral cell therapy, and more particularly, for improving viral and non-viral vector manufacturing yield and quality, for reducing transfection associated toxicity, for improving transposition from non-viral transposon vectors, for improving packaging titers from viral vectors, for improving expression of viral and non-viral vector encoded transgenes, and for eliminating antibiotic resistance marker gene transfer by viral and non-viral vectors.

Improved vector methods and compositions that utilize a Pol III-dependent origin of replication to replicate structured DNA sequences are disclosed.

Improved vector methods and compositions that utilize a Pol III-dependent origin of replication to replicate inverted repeat DNA sequences are disclosed.

Improved vector methods and compositions that utilize a Pol III-dependent origin of replication to replicate direct repeat DNA sequences are disclosed.

Improved vector methods and compositions that utilize a Poi III-dependent origin of replication to replicate homopolymeric repeat DNA sequences are disclosed.

Improved vector methods and compositions that utilize a Pol III-dependent origin of replication to replicate enhancer structured DNA sequences are disclosed.

Improved vector methods and compositions that utilize a Pol III-dependent origin of replication to replicate polyA repeat DNA sequences are disclosed.

Improved vector methods and compositions that utilize a Pol III-dependent origin of replication to replicate SV40 origin of replication DNA sequences are disclosed.

Improved vector methods and compositions that utilize a Pol III-dependent origin of replication to replicate Lentiviral LTR DNA sequences are disclosed.

Improved vector methods and compositions that utilize a Pol III-dependent origin of replication to replicate Retroviral LTR DNA sequences are disclosed.

Improved vector methods and compositions that utilize a Pol III-dependent origin of replication to replicate viral LTR DNA sequences are disclosed.

Improved vector methods and compositions that utilize a Pol III-dependent origin of replication to replicate AAV ITR DNA sequences are disclosed.

Improved vector methods and compositions that utilize a Pol III-dependent origin of replication to replicate transposon IR/DR DNA sequences are disclosed.

Improved vector methods and compositions that utilize a Pol III-dependent origin of replication to replicate Sleeping Beauty IR/DR DNA sequences are disclosed.

Improved vector methods and compositions that utilize a Pol III-dependent origin of replication to replicate Piggy Bac ITR DNA sequences are disclosed.

Improved vector methods and compositions that utilize a Pol III-dependent origin of replication to replicate CMV enhancer DNA sequences are disclosed.

Improved vector methods and compositions that utilize a Pol III-dependent origin of replication to replicate direct SV40 enhancer DNA sequences are disclosed.

Improved viral vector methods and compositions that utilize a Pol III-dependent origin of replication are disclosed.

Improved Lentiviral vector, Lentiviral envelope vector and Lentiviral packaging vector methods and compositions that utilize a Pol III-dependent origin of replication are disclosed.

Improved Retroviral vector, Retroviral envelope vector and Retroviral packaging vector methods and compositions that utilize a Pol III-dependent origin of replication are disclosed.

Improved AAV vector and AAV helper vector methods and compositions that utilize a Pol III-dependent origin of replication are disclosed.

Improved Adenoviral vector methods and compositions that utilize a Pol III-dependent origin of replication are disclosed.

Improved non-viral transposon and transposase vector methods and compositions that utilize a Pol III-dependent origin of replication are disclosed.

Improved non-viral Sleeping Beauty transposon and transposase vector methods and compositions that utilize a Pol III-dependent origin of replication are disclosed.

Improved non-viral PiggyBac transposon and transposase vector methods and compositions that utilize a Pol III-dependent origin of replication are disclosed.

Improved non-viral Tol2 transposon and transposase vector methods and compositions that utilize a Pol III-dependent origin of replication are disclosed.

Improved non-viral polyA containing mRNA vector methods and compositions that utilize a Pol III-dependent origin of replication are disclosed Improved viral vector methods and compositions with improved viral transducing unit production that utilize a Pol III-dependent origin of replication are disclosed.

Improved Lentiviral vector methods and compositions with improved viral transducing unit production that utilize a Pol III-dependent origin of replication are disclosed.

Improved Retroviral vector methods and compositions with improved viral transducing unit production that utilize a Pol III-dependent origin of replication are disclosed.

Improved AAV vector and AAV helper vector methods and compositions with improved viral transducing unit production that utilize a Pol III-dependent origin of replication are disclosed.

Improved non-viral transposon and transposase vector methods and compositions with improved transposition that utilize a Pol III-dependent origin of replication are disclosed.

Improved non-viral Sleeping Beauty transposon and transposase vector methods and compositions with improved transposition that utilize a Pol III-dependent origin of replication are disclosed.

Improved non-viral PiggyBac transposon and transposase vector methods and compositions with improved transposition that utilize a Pol III-dependent origin of replication are disclosed.

Improved non-viral Tol2 transposon and transposase vector methods and compositions with improved transposition that utilize a Pol III-dependent origin of replication are disclosed.

Improved viral vector methods and compositions with improved expression that utilize a Pol III-dependent origin of replication are disclosed.

Improved Lentiviral vector methods and compositions with improved expression that utilize a Pol III-dependent origin of replication are disclosed.

Improved Retroviral vector methods and compositions with improved expression that utilize a Pol III-dependent origin of replication are disclosed.

Improved AAV vector and AAV helper vector methods and compositions with improved expression that utilize a Pol III-dependent origin of replication are disclosed.

Improved non-viral transposon and transposase vector methods and compositions with improved expression that utilize a Pol III-dependent origin of replication are disclosed.

Improved non-viral Sleeping Beauty transposon and transposase vector methods and compositions with improved expression that utilize a Pol III-dependent origin of replication are disclosed.

Improved non-viral PiggyBac transposon and transposase vector methods and compositions with improved expression that utilize a Pol III-dependent origin of replication are disclosed.

Improved non-viral Tol2 transposon and transposase vector methods and compositions with improved expression that utilize a Pol III-dependent origin of replication are disclosed.

Improved viral vector methods and compositions with no antibiotic resistance marker gene transfer risk that utilize a Pol III-dependent origin of replication are disclosed.

Improved Lentiviral vector, Lentiviral envelope vector and Lentiviral packaging vector methods and compositions with no antibiotic resistance marker gene transfer risk that utilize a Pol III-dependent origin of replication are disclosed.

Improved Retroviral vector, Retroviral envelope vector and Retroviral packing vector methods and compositions with no antibiotic resistance marker gene transfer risk that utilize a Pol III-dependent origin of replication are disclosed.

Improved AAV vector and AAV helper vector methods and compositions with no antibiotic resistance marker gene transfer risk that utilize a Pol III-dependent origin of replication are disclosed.

Improved non-viral transposon and transposase vector methods and compositions with no antibiotic resistance marker gene transfer risk that utilize a Pol III-dependent origin of replication are disclosed.

Improved non-viral Sleeping Beauty transposon and transposase vector methods and compositions with no antibiotic resistance marker gene transfer risk that utilize a Pol III-dependent origin of replication are disclosed.

Improved non-viral PiggyBac transposon and transposase vector methods and compositions with no antibiotic resistance marker gene transfer risk that utilize a Pol III-dependent origin of replication are disclosed.

Improved non-viral Tol2 transposon and transposase vector methods and compositions with no antibiotic resistance marker gene transfer risk that utilize a Pol III-dependent origin of replication are disclosed.

Improved viral vector methods and compositions with reduced transfection associated toxicity that utilize a Pol III-dependent origin of replication are disclosed.

Improved Lentiviral vector methods and compositions with reduced transfection associated toxicity that utilize a Pol III-dependent origin of replication are disclosed.

Improved Retroviral vector methods and compositions with reduced transfection associated toxicity that utilize a Pol III-dependent origin of replication are disclosed.

Improved AAV vector and AAV helper vector methods and compositions with reduced transfection associated toxicity that utilize a Pol III-dependent origin of replication are disclosed.

Improved non-viral transposon and transposase vector methods and compositions with reduced transfection associated toxicity that utilize a Pol III-dependent origin of replication are disclosed.

Improved non-viral Sleeping Beauty transposon and transposase vector methods and compositions with reduced transfection associated toxicity that utilize a Pol III-dependent origin of replication are disclosed.

Improved non-viral PiggyBac transposon and transposase vector methods and compositions with reduced transfection associated toxicity that utilize a Pol III-dependent origin of replication are disclosed.

Improved non-viral Tol2 transposon and transposase vector methods and compositions with reduced transfection associated toxicity that utilize a Pol III-dependent origin of replication are disclosed.

Each of the above improvements and the improvements described below is, for example, relative to what is achieved in similar or identical circumstances, but with a different plasmid that does not include a Pol III-dependent original of replication.

One object of the invention is to provide improved viral and non-viral vector manufacturing yield.

Another object of the invention is to provide improved viral and non-viral vector manufacturing quality.

Another object of the invention is to provide viral vectors with improved packaging titers.

Another object of the invention is to provide non-viral transposon vectors with improved transposition.

Another object of the invention is to provide viral and non-viral vectors with improved expression of encoded transgenes.

Another object of the invention is to provide viral and non-viral vectors that eliminate antibiotic resistance marker gene transfer.

Another object of the invention is to provide viral and non-viral vectors with reduced transfection associated toxicity.

In one embodiment, the present technology provides a method for improving the replication of a covalently closed circular plasmid comprising the following steps: a) providing a covalently closed circular plasmid comprising: i) a Pol I-dependent origin of replication, and ii) an insert comprising a structured DNA sequence selected from the group consisting of inverted repeat sequence, direct repeat sequence, homopolymeric repeat sequence, eukaryotic origin of replication and eukaryotic promoter enhancer sequence, wherein the structured DNA sequence is located at a distance of less than 1000 bp from the Pol I-dependent origin of replication in the direction of replication; b) modifying the covalently closed circular recombinant molecule of a) such that the Pol I-dependent origin of replication is replaced with a Pol III-dependent origin of replication whereby the resultant Pol III-dependent origin of replication covalently closed circular plasmid has improved replication. In a further embodiment said Pol I-dependent origin of replication is selected from the group consisting of pUC origin, pMB1 origin, and ColE1 origin. In a further embodiment said Pol III-dependent origin of replication is an R6K gamma replication origin. In a further embodiment said Pol III-dependent origin of replication is an R6K gamma replication origin with at least 95% sequence identity to a sequence selected from the group consisting of SEQ ID NO:

1, SEQ ID NO: 2, SEQ ID NO: 3, SEQ ID NO: 4 and SEQ ID NO: 18. In a further embodiment said structured DNA sequence is selected from the group consisting of polyA repeat, SV40 origin of replication, viral LTR, Lentiviral LTR, Retroviral LTR, transposon IR/DR repeat, Sleeping Beauty transposon IR/DR repeat, AAV ITR, CMV enhancer, and SV40 enhancer. In a further embodiment said improved replication is selected from the group consisting of reduced production of replication intermediates and increased plasmid copy number.

In another embodiment, the present technology provides a method for improving the replication of a covalently closed circular plasmid comprising the following steps: a) providing a covalently closed circular plasmid comprising: i) a bacterial replication-selection region comprising a Pol I-dependent origin of replication and an antibiotic selectable marker, and ii) an insert comprising a structured DNA sequence selected from the group consisting of inverted repeat sequence, direct repeat sequence, homopolymeric repeat sequence, eukaryotic origin of replication and eukaryotic promoter enhancer sequence, wherein the structured DNA sequence is located at a distance of less than 1000 bp from the Pol I-dependent origin of replication in the direction of replication; b) modifying the covalently closed circular recombinant molecule of a) such that the antibiotic selectable marker is replaced with an RNA selectable marker and the Pol I-dependent origin of replication is replaced with a Pol III-dependent origin of replication, whereby the resultant Pol III-dependent origin of replication covalently closed circular plasmid has improved replication. In a further embodiment said Pol I-dependent origin of replication is selected from the group consisting of: pUC origin, pMB1 origin, and ColE1 origin. In a further embodiment said Pol III-dependent origin of replication is an R6K gamma replication origin. In a further embodiment said Pol III-dependent origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA selectable marker is an RNA-OUT RNA selectable marker that encodes an RNA-IN regulating RNA-OUT RNA with at least 95% sequence identity to SEQ ID NO: 6. In a further embodiment said bacterial replication-selection region comprising a Pol I-dependent origin of replication and an antibiotic selectable marker is replaced with a Pol III-dependent R6K, origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17. In a further embodiment said structured DNA sequence is selected from the group consisting of polyA repeat, SV40 origin of replication, viral LTR, Lentiviral LTR, Retroviral LTR, transposon IR/DR repeat, Sleeping Beauty transposon IR/DR repeat, AAV ITR, CMV enhancer, and SV40 enhancer. In a further embodiment said improved replication is selected from the group consisting of reduced production of replication intermediates, and increased plasmid copy number.

In one embodiment, the current technology provides an antibiotic marker free covalently closed circular recombinant DNA molecule comprising: a) an antibiotic marker free insert comprising a structured DNA sequence selected from the group consisting of inverted repeat sequence, direct repeat sequence, homopolymeric repeat sequence, eukaryotic origin of replication, and eukaryotic promoter enhancer sequence; b) a Pol III-dependent origin of replication comprising an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18; and c) an RNA-OUT RNA selectable marker comprising an RNA-IN regulating RNA-OUT functional variant with at least 95% sequence identity to a sequence selected from the group consisting of SEQ ID NO: 5, and SEQ ID NO: 7. In a further embodiment said R6K gamma replication origin and said RNA-OUT RNA selectable marker comprise a R6K origin-RNA-OUT RNA selectable marker bacterial replication-selection region with at least 95% sequence identity to a sequence selected from the group consisting of SEQ ID NO: 8, SEQ NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17. In a further embodiment said structured DNA sequence is selected from the group consisting of polyA repeat, SV40 origin of replication, viral LTR, Lentiviral LTR, Retroviral LTR, transposon IR/DR repeat, Sleeping Beauty transposon IR/DR repeat, AAV ITR, CMV enhancer, and SV40 enhancer. In a further embodiment said recombinant DNA molecule is selected from the group consisting of viral vector, Lentiviral vector, Retroviral vector, AAV vector, Ad vector, non-viral transposon vector, Sleeping Beauty transposon vector, PiggyBac transposon vector, Tol2 transposon vector, and polyA containing mRNA vector.

In one embodiment, the present technology provides a method for improving AAV vector viral transducing unit production from a covalently closed circular plasmid comprising the following steps: a) providing a covalently closed circular plasmid comprising: i) a 1 kb or larger bacterial replication-selection region comprising a Pol I-dependent origin of replication and an antibiotic selectable marker, and ii) an insert comprising a eukaryotic region selected from the group consisting of AAV vector, AAV rep cap vector, Ad helper vector, and Ad helper rep cap vector; b) modifying the covalently closed circular recombinant molecule of a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol III-dependent origin of replication covalently closed circular plasmid has improved AAV viral transducing unit production when transfected into mammalian cells. In a further embodiment said Pol I-dependent origin of replication is selected from the group consisting of: pUC origin, pMB1 origin, and ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NC): 12, SEQ ID NO: 13, SEQ ID NO: 14, SEQ ID NO: 15, SEQ ID NO: 16, and SEQ NO: 17.

In one embodiment, the current technology provides a method for improving Retroviral or Lentiviral vector viral transducing unit production from a covalently closed circular plasmid comprising the following steps: a) providing a covalently closed circular plasmid comprising: i) a 1 kb or larger bacterial replication-selection region comprising a Pol I-dependent origin of replication and an antibiotic selectable marker, and ii) an insert comprising a eukaryotic region selected from the group consisting of Retroviral vector, Lentiviral vector, Retroviral envelope vector, Lentiviral envelope vector, Retroviral packaging vector and Lentiviral packaging vector; and b) modifying the covalently closed circular recombinant molecule of a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol IR-dependent origin of replication covalently closed circular plasmid has improved viral transducing unit production when transfected into mammalian cells. In a further embodiment said Pol I-dependent origin of replication is selected from the group consisting of: pUC origin, pMB1 origin, and ColE1 origin. In a further embodiment said Pol III-dependent R6K, origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NO: 12, SEQ II) NO: 13, SEQ ID NO: 14, SEQ ID NO: 15, SEQ ID NO: 16, and SEQ ID NO: 17.

In one embodiment, the present invention contemplates a method for improving transposition from a covalently closed circular non-viral transposon plasmid comprising the following steps: a) providing a covalently closed circular plasmid comprising i) a 1 kb or larger bacterial replication-selection region comprising a Pol I-dependent origin of replication and an antibiotic selectable marker, and ii) an insert comprising a non-viral eukaryotic region selected from the group consisting of transposon vector, Sleeping Beauty transposon vector, Sleeping Beauty transposase vector, PiggyBac transposon vector, PiggyBac transposase vector, Tol2 transposon vector, Tol2 transposase vector; b) modifying the covalently closed circular recombinant molecule of (a) such that the 1 kb or larger bacterial replication-selection region comprising a Pol I-dependent origin of replication and an antibiotic selectable marker is replaced with an less than 1 kb Pol III-dependent R6K origin-RNA- OUT RNA selectable marker bacterial replication-selection region, whereby the resultant Pol III-dependent origin of replication covalently closed circular plasmid has improved transposition when transfected into mammalian cells. In a further embodiment said Pol I-dependent origin of replication is selected from the group consisting of: pUC origin, pMB1 origin, or ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17.

In one embodiment, current technology provides a method for improving expression from a covalently closed circular viral vector or non-viral transposon plasmid comprising the following steps: a) providing a covalently closed circular plasmid comprising: i) a 1 kb or larger bacterial replication-selection region comprising a Pol I-dependent origin of replication and an antibiotic selectable marker, and ii) an insert comprising a eukaryotic region selected from the group consisting of Lentiviral vector, Retroviral vector, and AAV vector or non-viral transposon vector; and b) modifying the covalently closed circular recombinant molecule of (a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol III-dependent origin of replication covalently closed circular plasmid has improved expression when transfected into mammalian cells. In a further embodiment said Pol I-dependent origin of replication is selected from the group consisting of pUC origin, pMB1 origin, and ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

In one embodiment, the present technology provides a method for eliminating antibiotic resistant marker gene transfer from a covalently closed circular viral vector plasmid comprising the following steps: a) providing a covalently closed circular plasmid comprising: i) a 1 kb or larger bacterial replication-selection region comprising a Pol I-dependent origin of replication and an antibiotic resistance marker, and ii) an insert comprising an antibiotic resistance marker free eukaryotic region selected from the group consisting of viral vector, Lentiviral vector, Lentiviral packaging vector, Lentiviral envelope vector Retroviral vector, Retroviral envelope vector, Retroviral packaging vector, AAV vector, AAV rep cap vector, Ad helper vector, and Ad helper rep cap vector; and b) modifying the covalently closed circular recombinant molecule of a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol III-dependent origin of replication covalently closed circular plasmid has no antibiotic resistance markers that could be packaged into Lentiviral, Retroviral or AAV transducing viral particles when transfected into mammalian cells. In a further embodiment said Pol I-dependent origin of replication is selected from the group consisting of: pUC origin, pMB1 origin, and ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K. origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

In one embodiment, the present technology provides a method for eliminating antibiotic resistant marker gene transfer from a covalently closed circular non-viral transposon plasmid comprising the following steps: a) providing a covalently closed circular plasmid comprising: i) a 1 kb or larger bacterial replication-selection region comprising a Pol. I-dependent origin of replication and an antibiotic resistance marker, and ii) an insert comprising an antibiotic resistance marker free eukaryotic region selected from the group consisting of non-viral transposon vector, non-viral transposase vector, Sleeping Beauty transposon vector, Sleeping Beauty transposase vector, PiggyBac transposon vector, PiggyBac transposase vector, Tol2 transposon vector, Tol2 transposase vector; and b) modifying the covalently closed circular recombinant molecule of a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol III-dependent origin of replication covalently closed circular plasmid has no antibiotic resistance markers that could be transposed into the genome when transfected into mammalian cells. In a further embodiment said Pol I-dependent origin of replication is selected from the group consisting of: pUC origin, pMB1 origin, and ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18, In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ NO: 14, SEQ ID NO: 15, SEQ ID NO: 16, and SEQ ID NO: 17.

In one embodiment, the present technology provides an antibiotic marker free covalently closed circular recombinant DNA molecule comprising: a) an antibiotic marker free insert comprising a eukaryotic region selected from the group consisting of Lentiviral vector, Lentiviral envelope vector, Lentiviral packaging vector, Retroviral vector, Retroviral envelope vector, Retroviral packaging vector, AAV vector, AAV rep cap vector, Ad helper vector, Ad helper rep cap vector, non-viral transposon vector, and non-viral transposase vector; b) a Pol III-dependent origin of replication comprising an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18; and c) an RNA-OUT RNA selectable marker comprising an RNA-IN regulating RNA-OUT functional variant with at least 95% sequence identity to a sequence selected from the group consisting of SEQ ID NO: 5, and SEQ ID NO: 7. In a further embodiment said R6K gamma replication origin and said RNA-OUT RNA selectable marker comprise a R6K origin-RNA-OUT RNA selectable marker bacterial replication-selection region with at least 95% sequence identity to a sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

In one embodiment, the present technology provides a method for reducing transfection associated toxicity from a covalently closed circular viral vector or non-viral transposon plasmid comprising: a) providing a covalently closed circular plasmid comprising: i) a 1 kb or larger bacterial replication-selection region comprising a Pol I-dependent origin of replication and an antibiotic selectable marker, and ii) an insert comprising a eukaryotic region selected from the group consisting of Lentiviral vector, Retroviral vector. AAV vector and non-viral transposon vector; modifying the covalently closed circular recombinant molecule of a) such that the 1 kb or larger bacterial replication-selection region comprising a Pol I-dependent origin of replication and an antibiotic selectable marker is replaced with an less than 1 kb Pol III-dependent R6K origin-RNA-OUT RNA selectable marker bacterial replication-selection region, whereby the resultant Pol III-dependent origin of replication covalently closed circular plasmid has reduced toxicity when transfected by transfection associated into mammalian cells. In a further embodiment said Pol I-dependent origin of replication is selected from the group consisting of: pUC origin, pMB1 origin, and ColE1 origin. In a further embodiment said Pol III-dependent R6K origin of replication is an R6K gamma replication origin with at least 95% sequence identity to a sequence selected from the group consisting of SEQ ID NO: 1, SEQ ID NO: 2, SEQ ID NO: 3, SEQ ID NO: 4 and SEQ ID NO: 18. In a further embodiment said RNA-OUT RNA selectable marker is an RNA-IN regulating RNA-OUT functional variant with at least 95% sequence identity to a sequence selected from the group consisting of SEQ ID NO: 5, and SEQ ID NO: 7. In a further embodiment said RNA-OUT RNA selectable marker is an RNA-OUT RNA selectable marker that encodes an RNA-IN regulating RNA-OUT RNA with at least 95% sequence identity to SEQ ID NO: 6. In a further embodiment said less than 1 kb Pol III-dependent R6K origin-RNA-OUT RNA selectable marker bacterial replication-selection region has at least 95% sequence identity to a sequence selected from the group consisting of SEQ ID NC): 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

The resultant Pol III-dependent replication origin plasmids have surprisingly improved manufacturing quality and yield than the parent pMB1, ColE1 or pBR322 derived replication origin expression plasmid vector.

Further objects and advantages of the invention will become apparent from a consideration of the drawings and ensuing description.

BRIEF DESCRIPTION OF THE FIGURES

FIGS. 1A-1F depict the R6K origin (FIGS. 1A, 1E, and 1F), RNA-OUT selectable marker (FIG. 1B), and 14 and 3 CpG R6K-RNA-OUT bacterial backbones (FIGS. 1C and 1D);

FIGS. 4A-4F depict Pol I-dependent pUC origin A60 polyA repeat encoding mRNA vectors (FIGS. 4A-4B), a Pol III-dependent R6K origin A60 polyA repeat encoding mRNA vector (FIG. 4C), Pol I-dependent pUC origin A99 polyA repeat encoding mRNA vectors (FIGS. 4D-4E), and a Pol III-dependent R6K origin A99 polyA repeat encoding mRNA vector (FIG. 4F).

Figure 1A:
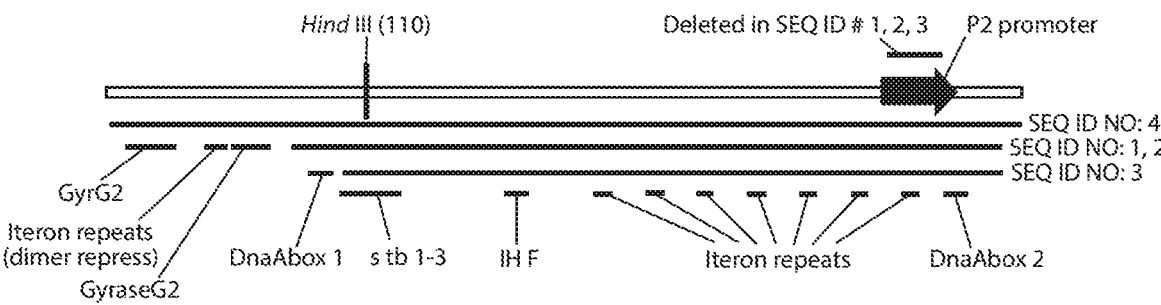

Table 1: pVAX1 mammalian expression vector spacer region (SR) derivatives expression level Table 2: NTC8685 mammalian expression vector spacer region (SR) derivatives expression level Table 3: Minicircle applications with various viral and non-viral vector platforms Table 4: pNTC multiple cloning site flanked R6K Origin-RNA-OUT selection marker vectors Table 5: SV40 origin Lentiviral vectors: pUC versus R6K origin shake flask production yields/quality Table 6: Sleeping Beauty Transposon vectors: pUC versus R6K origin shake flask production yields/quality Table 7: AAV vectors: pUC versus R6K origin shake flask production yields/quality Table 8: mRNA vectors: pUC versus R6K origin DH5α HyperGRO fermentation yields/quality Table 9: AAV helper vectors: pUC versus R6K origin plasmid production yields/quality SEQ ID NO:1: R6K gamma origin SEQ ID NO:2: 1 CpG R6K gamma origin SEQ ID NO:3: CpG free R6K gamma origin SEQ ID NO:4: Extended R6K gamma origin SEQ ID NO:5: RNA-OUT Selectable Marker SEQ ID NO:6: RNA-OUT antisense repressor RNA SEQ ID NO:7: 2 CpG RNA-OUT Selectable Marker SEQ ID NO:8: R6K gamma origin-RNA-OUT bacterial region flanked by NheI and KpnI restriction sites SEQ ID NO:9: 1 CpG R6K gamma origin-2 CpG RNA-OUT bacterial region flanked by NheI and KpnI restriction sites SEQ ID NO:10: pNTC-NP1 polylinker trpA R6K-RNA-OUT polylinker cloning cassette: EcoRI/HindIII SEQ ID NO:11: pNTC-NP2 polylinker trpA R6K-RNA-OUT polylinker cloning cassette: EcoRI/HindIII SEQ ID NO:12: pNTC-NP3 polylinker trpA R6K-RNA-OUT polylinker cloning cassette: EcoRI/HindIII SEQ ID NO:13: pNTC-NP4 polylinker trpA R6K-RNA-OUT polylinker cloning cassette: EcoRI/HindIII SEQ ID NO:14: pNTC-NP5 polylinker trpA R6K-RNA-OUT polylinker cloning cassette: KasI/HindIII SEQ ID NO:15: pNTC-NP6 polylinker trpA R6K-RNA-OUT polylinker cloning cassette: EcoRI/SacI SEQ ID NO:16: pNTC-NP7 polylinker trpA R6K-RNA-OUT polylinker cloning cassette: BssHII-BssHII SEQ ID NO:17: pNTC-3xCpG NP1 polylinker R6K-RNA-OUT polylinker cloning cassette: HindIII-EcoRI SEQ ID NO:18: R6K gamma origin (7 iteron)

SEQ ID NO:19: R6K gamma origin 22 bp iteron repeat

SEQ ID NO:20: R6K gamma origin 22 bp iteron repeat

SEQ ID NO:21: R6K gamma origin 22 bp iteron repeat

SEQ ID NO:22: R6K gamma origin 22 bp iteron repeat

SEQ ID NO:23: R6K gamma origin 22 bp iteron repeat

Definition of Terms

AAV vector: Adeno-associated virus vector, an episomal viral vector. Includes self-complementary (sc) Adeno-associated virus vectors (scAAV) and single-stranded (ss) Adeno-associated virus vectors (ssAAV)

AF: Antibiotic-free amp: Ampicillin ampR: Ampicillin Resistance gene

Antibiotic selectable marker: A gene that confers resistance to an antibiotic, e.g. ampicillin resistance gene, kanamycin resistance gene, chloramphenicol resistance gene, tetracycline resistance gene Approximately: As used herein, the term "approximately" or "about," as applied to one or more values of interest, refers to a value that is the same or similar to a stated reference value Bacterial region: Region of a plasmid vector required for propagation and selection in the bacterial host bp: basepairs ccc: Covalently Closed Circular cI: Lambda repressor cITs857: Lambda repressor further incorporating a C to T (Ala to Thr) mutation that confers temperature sensitivity. cITs857 is a functional repressor at 28-30° C. but is mostly inactive at 37-42° C. Also called cI857

Cat$^R$: Chloramphenicol resistance gene cmv: Cytomegalovirus dem methylation: *E. coli* methyltransferase that methylated the sequences CC(A/T)GG at the C5 position of the second cytosine DNA replicon: A genetic element that can replicate under its own control; examples include plasmids, cosmids, bacterial artificial chromosomes (BACs), bacteriophages, viral vectors and hybrids thereof

*E. coli: Escherichia coli*, a gram negative bacteria

EGFP: Enhanced green fluorescent protein

EP: Electroporation

Eukaryotic expression vector: A vector for expression of mRNA, protein antigens, protein therapeutics, shRNA, RNA or microRNA genes in a target eukaryotic organism using RNA Polymerase I, II or III promoters Eukaryotic region: The region of a plasmid that encodes eukaryotic sequences and/or sequences required for plasmid function in the target organism. This includes the region of a plasmid vector required for expression of one or more transgenes in the target organism including RNA Pol II enhancers, promoters, transgenes and polyA sequences. This also includes the region of a plasmid vector required for expression of one or more transgenes in the target organism using RNA Pol I or RNA Pol II promoters, RNA Pol I or RNA Pol III expressed transgenes or RNAs. The eukaryotic region may optionally include other functional sequences, such as eukaryotic transcriptional terminators, supercoiling-induced DNA duplex destabilized (SIDD) structures, S/MARs, boundary elements, etc. In a Lentiviral or Retroviral vector, the eukaryotic region contains flanking direct repeat LTRs, in a AAV vector the eukaryotic region contains flanking inverted terminal repeats, while in a Transposon vector the eukaryotic region contains flanking transposon inverted terminal repeats or IR/DR termini (e.g. Sleeping Beauty). In genome integration vectors, the eukaryotic region may encode homology arms to direct targeted integration Exon: A nucleotide sequence encoded by a gene that is transcribed and present within a mature mRNA product after RNA splicing to remove introns has been completed Expression vector: A vector for expression of mRNA, protein antigens, protein therapeutics, shRNA, RNA or microRNA genes in a target organism.

g: Gram, kg for kilogram gene of interest: gene to be expressed in the target organism. Includes mRNA genes that encode protein or peptide antigens, protein or peptide therapeutics, and mRNA, shRNA, RNA or microRNA that encode RNA therapeutics, and mRNA, shRNA, RNA or microRNA that encode RNA vaccines, etc.

Hr(s): Hour(s)

ID: Intradermal

IM: Intramuscular immune response: Antigen reactive cellular (e.g. antigen reactive T cells) or antibody (e.g. antigen reactive IgG) responses Introit A nucleotide sequence encoded by a gene that is transcribed and subsequently removed from a mature mRNA product by RNA splicing IR/OR: Inverted Repeats which are each Directly Repeated twice, For example, Sleeping Beauty transposon IR/DR repeats Iteron: Directly repeated DNA sequences in a origin of replication that are required for replication initiation. R6K origin iteron repeats are 22 bp ITR: Inverted Terminal Repeat kan: Kanamycin kanR: Kanamycin Resistance gene Kd: Kilodalton kozak sequence: Optimized consensus DNA sequence gccRccATG (R=G or A) immediately upstream of an ATG start codon that ensures efficient translation initiation. A SalI site (GTCGAC) immediately upstream of the ATG start codon (GTCGACATG) is an effective kozak sequence Lentiviral vector: Integrative viral vector that can infect dividing and non-dividing cells. Also call Lentiviral transfer plasmid. Plasmid encodes Lentiviral LTR flanked expression unit. Transfer plasmid is transfected into production cells along with Lentiviral envelope and packaging plasmids required to make viral particles Lentiviral envelope vector: Plasmid encoding envelope glycoprotein Lentiviral packaging vector: One or two plasmids that express gag, pol and Rev functions required to package the Lentiviral transfer vector minicircle: Covalently closed circular plasmid derivatives in which the bacterial region has been removed from the parent plasmid by in vivo or in vitro site-specific recombination or in vitro restriction digestion/ligation. Minicircle vectors are replication incompetent in bacterial cells mRNA: Messenger RNA mSEAP: Murine secreted alkaline phosphatase NA: Not Applicable Nanoplasmid™ vector: Vector combining an RNA selectable marker with a R6K, ColE2. or ColE2 related replication origin. For example, NTC9385C, NTC9685C, NTC9385R, NTC9685R vectors and modifications described in Williams, *Supra,* 2014 and included herein by reference NTC8385: NTC8385, NTC8485 and NTC8685 plasmids are antibiotic-free pUC origin vectors that contain a short RNA (RNA-OUT) selectable marker instead of an antibiotic resistance marker such as kanR. The creation and application of these RNA-OUT based antibiotic-free vectors are described in Williams, J A 2008 World Patent Application WO2008153733 and included herein by reference NTC8485: NTC8485 is an antibiotic-free pUC origin vector that contains a short RNA (RNA-OUT) selectable marker instead of an antibiotic resistance marker such as kanR. The creation and application of NTC8485 is described in Williams, J A. 2010 US Patent Application 20100184158 and included herein by reference NTC8685: NTC8685 is an antibiotic-free pUC origin vector that contains a short RNA (RNA-OUT) selectable marker instead of an antibiotic resistance marker such as kanR. The creation and application of NTC8685 is described in Williams, *Supra,* 2010 and included herein by reference NTC9385R: The NTC9385R Nanoplasmid™ vector described in Williams, *Supra,* 2014 included herein by reference has a spacer region encoded NheI-trpA terminator-R6K origin RNA-OUT-KpnI bacterial region (SEQ ID NO:8) linked through the flanking NheI and KpnI sites to the eukaryotic region.

OD$_{600}$: optical density at 600 nm

PAS: Primosomal assembly site, Priming of DNA synthesis on a single stranded. DNA ssi site. ØX174 type PAS: DNA hairpin sequence that binds priA, which, in turn, recruits the remaining proteins to form the preprimosome [priB, dnaT, recruits dnaB (delivered by dnaC)], which then also recruits primase (dnaG), which then, finally, makes a short RNA substrate for DNA polymerase I. ABC type PAS: DNA hairpin binds dnaA, recruits dnaB (delivered by dnaC) which then also recruits primase (dnaG), which then, finally, makes a short RNA substrate for DNA polymerase I. For example, the R6K plasmid CpG free ssiA primosomal assembly site or alternative ØXL74 type or ABC type primosomal assembly sites PAS-BH: Primosomal assembly site on the heavy (leading) strand PAS-BH region: pBR322 origin region between ROP and PAS-BL (approximately pBR322 2067-2351)

PAS-BL: Primosomal assembly site on the light (lagging) strand

PBS: Phosphate buffered Saline

PCR: Polymerase Chain Reaction pDNA: Plasmid DNA

PiggyBac Transposon: PB transposon. A transposon system that integrates an ITR flanked PB transposon into the genome by a simple cut and paste mechanism mediated by PB transposase. The transposon vector typically contains a promoter-transgene-polyA expression cassette between the PB LTRs which is excised and integrated into the genome pINT pR pL vector: The pINT pR pL att$_{HK022}$ integration expression vector is described in Luke et al., 2011 *Mol Biotechnol* 47:43 and included herein by reference. The target gene to be expressed is cloned downstream of the pL promoter. The vector encodes the temperature inducible cI857 repressor, allowing heat inducible target gene expression P$_L$ promoter: Lambda promoter left. P$_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues P$_L$ (OL1 G to T) promoter: Lambda promoter left. P$_L$ is a strong promoter that is repressed by the cI repressor binding to OL1, OL2 and OL3 repressor binding sites. The temperature sensitive cI857 repressor allows control of gene expression by heat induction since at 30° C. the cI857 repressor is functional and it represses gene expression, but at 37-42° C. the repressor is inactivated so expression of the gene ensues. The cI repressor binding to OL1 is reduced by the OL1 G to T mutation resulting in increased promoter activity at 30° C. and 37-42° C. as described in Williams, *Supra*, 2014.

Plasmid: An extra chromosomal DNA molecule separate from the chromosomal DNA which is capable of replicating independently from the chromosomal DNA Plasmid copy number: the number of copies of a plasmid per cell. Increases in plasmid copy number increase plasmid production yield Pol: Polymerase Pol I: *Escherichia coli* DNA Polymerase Pol I dependent origin of replication: A replication origin that requires Pol I, for example the pMB1, ColE1 or pBR322 or derivatives such as the high copy pUC origin. For these origins the RNAII primer forms an RNA: DNA R-loop that is cleaved by RNase H to create a primer for DNA pol I directed DNA synthesis. DNA synthesis then converts to DNA pol III. Numerous additional Pol I dependent replication origins are known in the art, many of which are summarized in del Solar et al., 1998 *Microbiol. Mol. Biol. Rev* 62:434-464 which is included herein by reference Pol III: *Escherichia coli* DNA Polymerase Ill Pol III dependent origin of replication: A replication origin that doesn't require Pol I, for example the rep protein dependent R6K gamma replication origin. Numerous additional Pol III dependent replication origins are known in the art, many of which are summarized in del Solar et al., *Supra*, 1998 which is included herein by reference polyA: Polyadenylation signal or site. Polyadenylation is the addition of a poly(A) tail to an RNA molecule. The polyadenylation signal contains the sequence motif recognized by the RNA cleavage complex. Most human polyadenylation signals contain an AAUAAA motif and conserved sequences 5' and 3' to it. Commonly utilized polyA signals are derived from the rabbit β globin, bovine growth hormone, SV40 early, or SV40 late polyA signals pUC origin: pBR322-derived replication origin, with G to A transition that increases copy number at elevated temperature and deletion of the ROP negative regulator pUC free: Plasmid that does not contain the pUC origin. Non-replicative fragments of the pUC origin may be included, for example the RNAI selectable marker pUC plasmid: Plasmid containing the pUC origin R6K plasmid: NTC9385R, NTC9685R, NTC9385R2-O1, NTC9385R2-O2, NTC9385R2a-O1, NTC9385R2a-O2, NTC9385R2b-O1, NTC9385R2b-O2, NTC9385Ra-O1, NTC9385Ra-O2, NTC9385RaF, and NTC9385RbF vectors as well as modifications and alternative vectors containing a R6K replication origin that were described in Williams, *Supra,* 2014 and included herein by reference. Alternative R6K vectors known in the art including, but not limited to, pCOR vectors (Gencell), pCpGfree vectors (Invivogen), and CpG free University of Oxford vectors including pGM169

R6K replication origin: a region which is specifically recognized by the R6K Rep protein to initiate DNA replication. Includes but not limited to R6K gamma replication origin sequence disclosed as SEQ ID NO:1, SEQ ID NO:2 SEQ ID NO:4, and SEQ ID NO:18. Also includes CpG free versions (e.g. SEQ ID NO:3) as described in Drocourt et al., U.S. Pat. No. 7,244,609 and incorporated herein by reference R6K replication origin-RNA-OUT bacterial region: Contains a R6K replication origin for propagation and the RNA-OUT selectable marker (e.g. SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17)

Rep: Replication

Replication intermediates: Linear DNA fragments resulting from premature termination of plasmid replication Rep protein dependent plasmid: A plasmid in which replication is dependent on a replication (Rep) protein provided in Trans. For example, R6K replication origin, ColE2-P9 replication origin and ColE2 related replication origin plasmids in which the Rep protein is expressed from the host strain genome. Numerous additional Rep protein dependent plasmids are known in the art, many of which are summarized in del Solar et al., *Supra,* 1998 which is included herein by reference Retroviral vector: Integrative viral vector that can infect dividing cells. Also call transfer plasmid. Plasmid encodes Retroviral LTR flanked expression unit. Transfer plasmid is transfected into production cells along with envelope and packaging plasmids required to make viral particles Retroviral envelope vector: Plasmid encoding envelope glycoprotein Retroviral packaging vector: Plasmid that encodes Retroviral gag, pol genes required to package the Retroviral transfer vector RNA-IN: Insertion sequence 10 (IS10) encoded RNA-IN, an RNA complementary and antisense to a portion of RNA RNA-OUT. When RNA-IN is cloned in the untranslated leader of a mRNA, annealing of RNA-IN to RNA-OUT reduces translation of the gene encoded downstream of RNA-IN RNA-IN regulated selectable marker: A genomically expressed RNA-IN regulated selectable marker. In the presence of plasmid borne RNA-OUT antisense repressor RNA (SEQ ID NO:6), expression of a protein encoded downstream of RNA-IN is repressed. An RNA-IN regulated selectable marker is configured such that RNA-IN regulates either 1) a protein that is lethal or toxic to said cell per se or by generating a toxic substance (e.g. SacB), or 2) a repressor protein that is lethal or toxic to said bacterial cell by repressing the transcription of a gene that is essential for growth of said cell (e.g. murA essential gene regulated by RNA-IN tetR repressor gene). For example, genomically expressed RNA-IN-SacB cell lines for RNA-OUT plasmid selection/propagation are described in Williams, *Supra,* 2008 and included herein by reference. Alternative selection markers described in the art may be substituted for SacB RNA-OUT: Insertion sequence 10 (IS10) encoded RNA-OUT, an antisense RNA that hybridizes to, and reduces translation of, the transposon gene expressed downstream of RNA-IN. The sequence of the RNA-OUT RNA (SEQ ID NO:6) and complementary RNA-IN SacB genomically expressed RNA-IN-SacB cell lines can be modified to incorporate alternative functional RNA-IN/RNA-OUT binding pairs such as those described in Mutalik et al., 2012. *Nat Chem Biol* 8:447, including, but not limited to, the RNA-OUT A08/RNA-IN S49 pair, the RNA-OUT A08/RNA-IN S08 pair, and CpG free modifications of RNA-OUT A08 that modify the CG in the RNA-OUT 5' TTCGC sequence to a non-CpG sequence. An example of a CpG free RNA-OUT selection marker, in which the two CpG motifs in the RNA-OUT RNA (one of which is present in the RNA-IN complementary region) are removed, was described in Williams 2015. Replicative minicircle vectors with improved expression. US Patent Application US 2015/0275221 and included herein by reference. A multitude of alternative substitutions to remove the two CpG motifs (mutating each CpG to either CpA, CpC, CpT, ApG, GpG, or TpG) may be utilized to make a CpG free RNA-OUT RNA-OUT Selectable marker: An RNA-OUT selectable marker DNA fragment including *E. coli* transcription promoter and terminator sequences flanking an RNA-OUT RNA. An RNA-OUT selectable marker, utilizing the RNA-OUT promoter and terminator sequences, that is flanked by DraIII and KpnI restriction enzyme sites, and designer genomically expressed RNA-IN-SacB cell lines for RNA-OUT plasmid propagation, are described in Williams, *Supra,* 2008 and included herein by reference. The RNA-OUT promoter and terminator sequences in SEQ ID NO: 5 that flank the RNA-OUT RNA (SEQ ID NO:6; FIG. 1B) may be replaced with heterologous promoter and terminator sequences. For example, the RNA-OUT promoter may be substituted with a CpG free promoter known in the art, for example the I-EC2K promoter or the P5/6 5/6 or P5/6 6/6 promoters described in Williams, *Supra,* 2008 and included herein by reference. A 2 CpG RNA-OUT selectable marker in which the two CpG motifs in the RNA-OUT promoter are removed is given as SEQ ID NO: 7. An example of a CpG free RNA-OUT transcription unit, in which the two CpG motifs in the RNA-OUT RNA (one of which is present in the RNA-IN complementary region) and the two CpG motifs in the RNA-OUT promoter are removed was described in Williams, *Supra,* 2015 and included herein by reference. Vectors incorporating CpG free RNA-OUT selectable marker may be selected for sucrose resistance using the RNA-IN-SacB cell lines for RNA-OUT plasmid propagation described in Williams, *Supra,* 2008. Alternatively, the RNA-IN sequence in these cell lines can be modified to incorporate the 1 bp change needed to perfectly match the CpG free RNA-OUT region complementary to RNA-IN.

RNA polymerase II promoter: Promoter that recruits RNA Polymerase II to synthesize mRNAs, most small nuclear RNAs and microRNAs. For example, constitutive promoters such as the human or murine CMV promoter, elongation factor 1 (EF1) promoter, the chicken β-actin promoter, the β-actin promoter from other species, the elongation factor-1 α (EF1 α) promoter, the phosphoglycerokinase (PGK) promoter, the Rous sarcoma virus (RSV) promoter, the human serum albumin (SA) promoter, the spleen focus-forming virus (SFFV) promoter, the α-1 antitrypsin (AAT) promoter, the thyroxine binding globulin (TBG) promoter, the cytochrome P450 2E1 (CYP2E1) promoter, etc. The vectors may also utilize combination promoters such as the chicken β-actin/CMV enhancer (CAG) promoter, the human or murine CMV-derived enhancer elements combined with the elongation factor 1α (EF1α) promoters, CpG free versions of the human or murine CMV-derived enhancer elements combined with the elongation factor 1α (EF1α) promoters the albumin promoter combined with an α-fetoprotein MERII enhancer, etc., or the diversity of tissue specific or inducible promoters know in the art such as the muscle specific promoters muscle creatine kinase (MCK), and C5-12 or the liver-specific promoter apolipoprotein A-I (ApoAI), etc.

RNA polymerase III promoter: Promoter that recruits RNA Polymerase III to synthesize tRNAs, 5S ribosomal RNA, and other small RNAs. For example, Class I promoters such as the 5s rRNA promoter, Class II promoter such as tRNA promoters, Class III promoters such as the U6 small nuclear RNA promoter or the H1 nuclear RNase P promoter, etc.

RNA selectable marker: An RNA selectable marker is a plasmid borne expressed non-translated RNA that regulates a chromosomally expressed target gene to afford selection. This may be a plasmid borne nonsense suppressing tRNA that regulates a nonsense suppressible selectable chromosomal target as described by Crouzet J and Soubrier F 2005 U.S. Pat. No. 6,977,174 included herein by reference. This may also be a plasmid borne antisense repressor RNA, a non limiting list included herein by reference includes RNA-OUT that represses RNA-IN regulated targets (Williams, *Supra,* 2008), pMB1 plasmid origin encoded RNAI that represses RNAII regulated targets (Grabherr R, Pfaffenzeller I. 2006 US patent application US20060063232; Cranenburgh R M. 2009; U.S. Pat. No. 7,611,883), IncB plasmid pMU720 origin encoded RNAI that represses RNA II regulated targets (Wilson I W, Siemering K R, Praszkier J, Pittard A J. 1997. *J Bacteriol* 179:742-53), ParB locus Sok of plasmid R1 that represses Hok regulated targets, Flm locus FlmB of F plasmid that represses flmA regulated targets (Morsey M A, 1999 U.S. Pat. No. 5,922,583). An RNA selectable marker may be another natural antisense repressor RNAs known in the art such as those described in Wagner E G H, Altuvia S, Romby P. 2002. *Adv Genet* 46:361-98 and Franch T, and Gerdes K. 2000. *Current Opin Microbial* 3:159-64. An RNA selectable marker may also be an engineered repressor RNAs such as synthetic small RNAs expressed SgrS, MicC or MicF scaffolds as described in Na D, Yoo S M, Chung H, Park H, Park J H, Lee S Y. 2013. *Nat Biotechnot* 31:170-4. An RNA selectable marker may also be an engineered repressor RNA as part of a selectable marker that represses a target RNA fused to a target gene to be regulated such as SacB as described in Williams, *Supra,* 2015

ROP: Repressor of primer

RSM: RNA selectable marker

SacB: Structural gene encoding *Bacillus subtilis* levansucrase. Expression of SacB in gram negative bacteria is toxic in the presence of sucrose SD: Standard deviation SEAP: Secreted alkaline phosphatase Selectable marker: A selectable marker, for example a kanamycin resistance gene or an RNA selectable marker Selection marker: A selectable marker, for example a kanamycin resistance gene or an RNA selectable marker SIDD: supercoiling-induced DNA duplex destabilized (SIDD) structures. These sites, when incorporated into a vector, may alter the susceptibility of other sequences within the vector to be destabilized. This can alter function. For example, addition of a SIDD site to an expression vector may reduce the helical destabilization of a promoter. This may increase or decrease promoter activity, depending on the promoter since some promoters have increased expression with promoter helical destabilization, while others will have reduced expression with promoter helical destabilization shRNA: Short hairpin RNA S/MAR: Scaffold/matrix attached region. Eukaryotic sequences that mediate DNA attachment to the nuclear matrix Sleeping Beauty Transposon: SB transposon. A transposon system that integrates an IR/DR flanked SB transposon into the genome by a simple cut and paste mechanism mediated by SB transposase. The transposon vector typically contains a promoter-transgene-polyA expression cassette between the IR/DRs which is excised and integrated into the genome Spacer region: As used herein, spacer region is the region linking the 5' and 3' ends of the eukaryotic region sequences. The eukaryotic region 5' and 3' ends are typically separated by the bacterial replication origin and bacterial selectable marker in plasmid vectors (bacterial region so many spacer regions consist of the bacterial region. In Pol III dependent origin of replication vectors of the invention, this spacer region preferably is less than 1000 bp SR: Spacer region.

ssi: Single stranded initiation sequences

Structured DNA sequence: As used herein, a DNA sequence that is capable of forming replication inhibiting secondary structures (Mirkin and Mirkin, 2007. *Microbiology and Molecular Biology Reviews* 71:13-35). This includes but is not limited to inverted repeats, palindromes, direct repeats, IR/DRs, homopolymeric repeats or repeat containing eukaryotic promoter enhancers, or repeat containing eukaryotic origin of replications.

SV40 origin: Simian Virus 40 genomic DNA that contains the origin of replication SV40 enhancer: Simian Virus 40 genomic DNA that contains the 72 bp and optionally the 21 bp enhancer repeats target antigen: Immunogenic protein or peptide epitope, or combination of proteins and epitopes, against which an immune response can be mounted. Target antigens may by derived from a pathogen for infectious disease or allergy applications or derived from a host organism for applications such as cancer, allergy, or autoimmune diseases. Target antigens are well defined in the art. Some examples are described in Williams, *Supra,* 2008 and are included herein by reference TE buffer: A solution containing approximately 10 mM Tris pH 8 and 1 mM EDTA TetR: Tetracycline resistance gene Tol2 Transposon: A transposon system that integrates an ITR flanked Tol2 transposon into the genome by a simple cut and paste mechanism mediated by Tol2 transposase. The transposon vector typically contains a promoter-transgene-polyA expression cassette between the Tol2 ITRs which is excised and integrated into the genome Transcription terminator: Bacterial: A DNA sequence that marks the end of a gene or operon for transcription. This may be an intrinsic transcription terminator or a Rho-dependent transcriptional terminator. For an intrinsic terminator, such as the trpA terminator, a hairpin structure forms within the transcript that disrupts the mRNA-DNA-RNA polymerase ternary complex. Alternatively, Rho-dependent transcriptional terminators require Rho factor, an RNA helicase protein complex, to disrupt the nascent mRNA-DNA-RNA polymerase ternary complex. Eukaryotic: PolyA signals are not 'terminators', instead internal cleavage at PolyA sites leaves an uncapped 5' end on the 3' UTR RNA for nuclease digestion. Nuclease catches up to RNA Pol II and causes termination. Termination can be promoted within a short region of the poly A site by introduction of RNA Pol II pause sites (eukaryotic transcription terminator). Pausing of RNA Pol II allows the nuclease introduced into the 3' UTR mRNA after PolyA cleavage to catch up to RNA Pol II at the pause site. A nonlimiting list of eukaryotic transcription terminators know in the art include the C2x4 and the gastrin terminator. Eukaryotic transcription terminators may elevate mRNA levels by enhancing proper 3'-end processing of mRNA transfection: Method to deliver nucleic acids into cells [e.g. poly(lactide-co-glycolide) (PLGA), ISCOMs, liposomes, niosomes, virosomes, block copolymers, Plutonic block copolymers, chitosan, and other biodegradable polymers, microparticles, microspheres, calcium phosphate nanoparticles, nanoparticles, nanocapsules, nanospheres, poloxamine nanospheres, electroporation, nucleofection, piezoelectric permeabilization, sonoporation, iontophoresis, ultrasound, SQZ high speed cell deformation mediated membrane disruption, corona plasma, plasma facilitated delivery, tissue tolerable plasma, laser microporation, shock wave energy, magnetic fields, contactless magnetopermeabilization, gene gun, microneedles, microdermabrasion, hydrodynamic delivery, high pressure tail vein injection, etc] as known in the art and included herein by reference Transgene: Gene of interest that is cloned into a vector for expression in a target organism Transposase vector: A vector which encodes a transposase Transposon vector: A vector which encodes a transposon which is a substrate for transposase mediated gene integration ts: Temperature sensitive μg: Microgram μl: Microliter UTR: Untranslated region of a mRNA (5' or 3' to the coding region)

Vector: A gene delivery vehicle, including viral (e.g. Alphavirus, Poxvirus, Lentivirus, Retrovirus, Adenovirus, Adenovirus related virus, etc.) and non-viral (e.g. plasmid, MIDGE, transcriptionally active PCR fragment, minicircles, bacteriophage, etc.) vectors. These are well known in the art and are included herein by reference Vector backbone: Eukaryotic region and bacterial region of a vector, without the transgene or target antigen coding region

DETAILED DESCRIPTION OF THE PREFERRED EMBODIMENTS

The current technology relates generally to short <1 kb bacterial region plasmid DNA vector methods and compositions that improve plasmid manufacture yield and quality, reduce transfection associated toxicity, and increase transgene expression. The current technology can be practiced to improve expression and manufacturing of vectors such as non-viral vectors (transposon vector, transposase vector, Sleeping Beauty transposon vector, Sleeping Beauty transposase vector, PiggyBac transposon vector, PiggyBac transposase vector, expression vector, etc.) and viral vectors (e.g. AAV vector, AAV rep cap vector, AAV helper vector, Ad helper vector, Lentivirus vector, Lentiviral envelope vector, Lentiviral packaging vector, Retroviral vector, Retroviral envelope vector, Retroviral packaging vector, etc.).

Improved plasmid expression is defined herein as improved transgene expression level and/or expression duration in vitro or in vivo compared to a transgene encoding plasmid containing a bacterial region encoding the pUC replication origin. It is to be understood that all references cited herein are incorporated by reference in their entirety.

The methods of plasmid modification of the present current technology have been surprisingly found to provide a solution to provide short spacer region vectors containing structured DNA sequences with efficient high yield manufacture.

As used herein, the term "sequence identity" refers to the degree of identity between any given query sequence, e.g. SEQ ID NO: 2, and a subject sequence. A subject sequence may, for example, have at least 90 percent, at least 95 percent, or at least 99 percent sequence identity to a given query sequence. To determine percent sequence identity, a query sequence (e.g. a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., 2003 *Nucleic Acids Res.,* 31:3497-500. In a preferred method, the sequence alignment program (e.g. ClustalW) calculates the best match between a query and one or more subject sequences, and aligns them so that identities, similarities, and differences can be determined. Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Figure 1B:
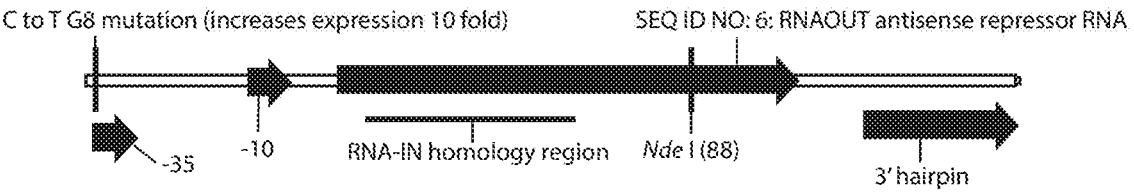
Figure 1C:
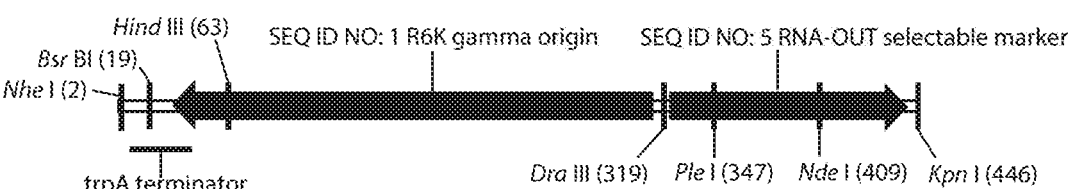
Figure 1D:
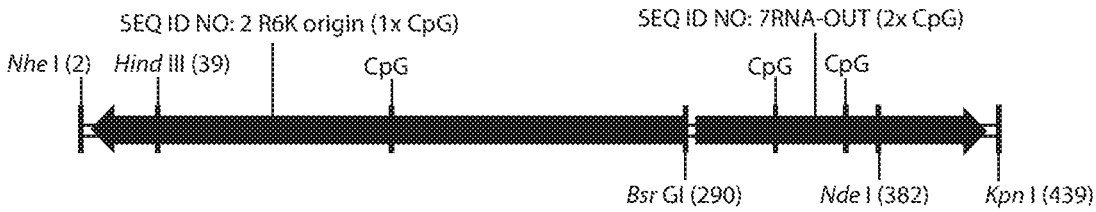
Figure 2A:
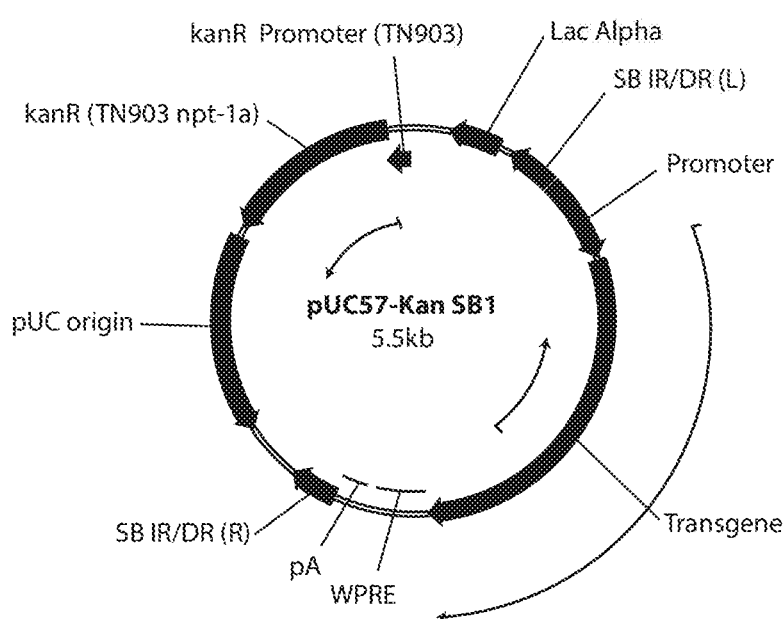
FIGS. 2A-2B depict a Pol I-dependent pUC origin Sleeping Beauty transposon vector (FIG. 2A) and a Pol III-dependent R6K origin Sleeping Beauty transposon vector (FIG. 2B)
Figure 2B:
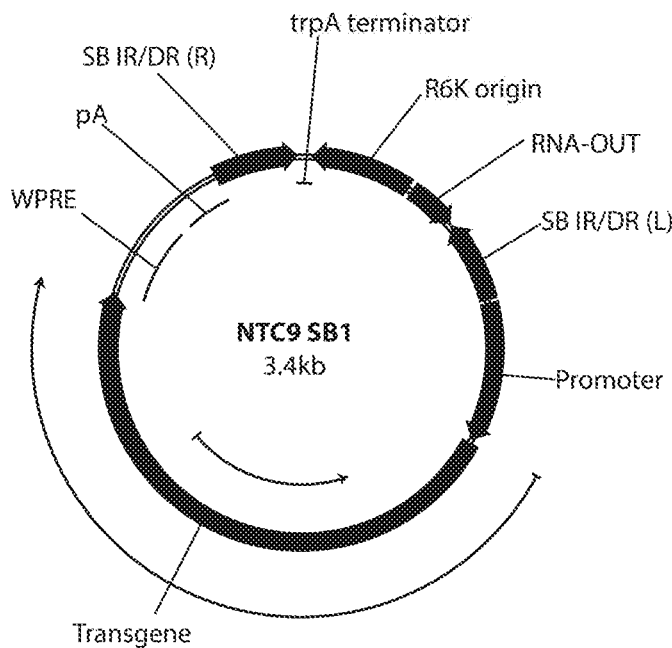

Turning now to the drawings, FIGS. 1A-1F show annotated maps of: FIG. 1A) R6K. origin with the locations of the 22 bp iteron repeats, DnaA boxes 1 and 2, and the regions included in the SEQ ID NO: 1, 2, 3, and 4 R6K origins; FIG. 1B) SEQ ID NO: 5 RNA-OUT selectable marker with the locations of the RNA-OUT promoter −35 and −10 elements, SEQ ID NO: 6 RNA OUT antisense RNA with RNA-IN complementary homology region and RNA-OUT terminator 3' hairpin; FIG. IC) 14 CpG R6K-RNA-OUT bacterial backbone composed of SEQ ID NO: 1 R6K replication origin and SEQ ID NO: 5 RNA-OUT selectable marker including the trpA bacterial terminator upstream of the R6K origin and flanked by NheI and KpnI cloning sites; FIG. 1D) 3 CpG R6K-RNA-OUT bacterial backbone composed of SEQ ID NO: 2 1x CpG R6K replication origin and SEQ ID NO: 7 2x CpG RNA-OUT selectable marker flanked by NheI and KpnI cloning sites; FIG. 1E) R6K origin from SEQ ID NO: 1, with locations of the 6 iterons highlighted. The individual 22 bp iteron repeat sequences are shown below the origin map; and FIG. 1F) R6K origin from SEQ ID NO: 18, with locations of the 7 herons highlighted. The individual 22 bp iteron repeat sequences are shown below the origin map. In this example 7 iteron vector iteron 5 has been tandemly duplication; however, a 7 iteron vector of the invention can be obtained by tandem duplication of any of iterons 1, 2, 3, 4, 5 or 6, FIGS. 2A-2B show annotated maps of: FIG. 2A) Pol I-dependent pUC origin-Kanamycin selection Sleeping Beauty transposon vector pUC57-Kan SB1 (see Table 6); and FIG. 2B) Pol III-dependent R6K origin-RNA-OUT antibiotic free selection Sleeping Beauty transposon vector NTC9 SB1 (see Table 6). The locations of the left and right Sleeping Beauty IR/DR relative to the bacterial backbone replication origins and selection markers are shown.

Figure 3A:
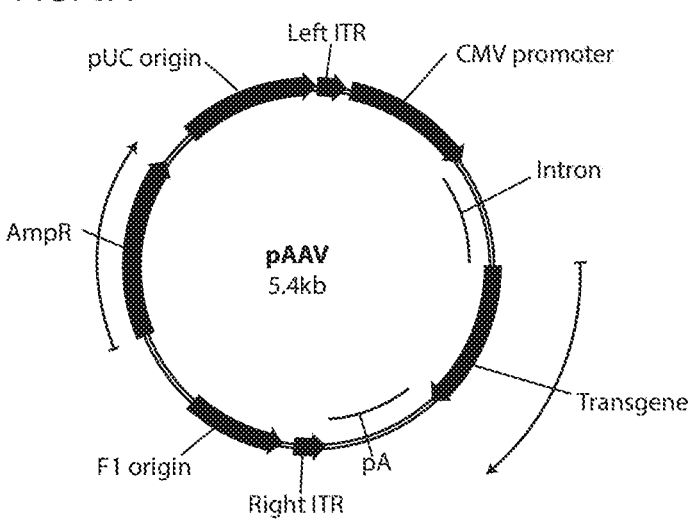
FIGS. 3A-3C depict Pol I-dependent pUC origin AAV vectors (FIGS. 3A and 3B) and a Pol III-dependent R6K origin AAV vectors (FIG. 3C)
Figure 3B:
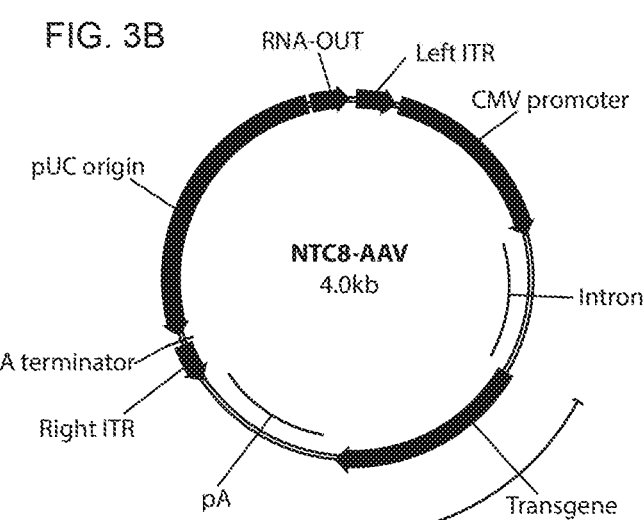
Figure 3C:
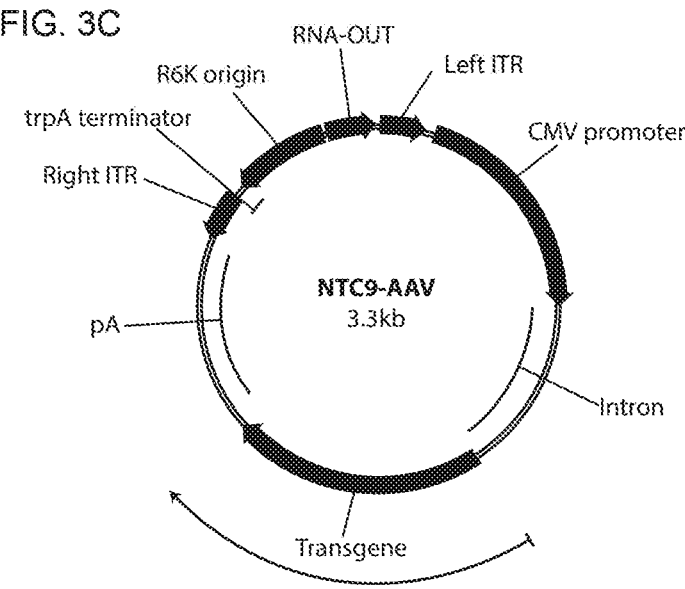

FIGS. 3A-3C show annotated maps of: FIG. 3A) Pol I-dependent pUC origin-Ampicillin selection AAV vector pAAV (see Table 7); FIG. 3B) Pol I-dependent pUC origin-RNA-OUT antibiotic free selection AAV vector NTC8-AAV (see Table 7); and FIG. 3C) Pol III-dependent R6K origin-RNA-OUT antibiotic free selection AAV vector NTC9-AAV (see Table 7). The locations of the left and right AAV ITRs relative to the bacterial backbone replication origins and selection markers are shown.

FIGS. 4A-4F show annotated maps of: FIG. 4A) Pol I-dependent pUC origin-Ampicillin selection A60 polyA repeat encoding mRNA vector pGEM4Z T7 A60 pA (see Table 8); FIG. 4B) Pol I-dependent pUC origin-RNA-OUT antibiotic free selection A60 polyA repeat encoding mRNA vector NTC8-T7 A60 pA (see Table 8); FIG. 4C) Pol III-dependent R6K origin-RNA-OUT antibiotic free selection A60 polyA repeat encoding snRNA vector NTC9-T7 A60 pA (see Table 8); FIG. 4D) Pol I-dependent pUC origin-Ampicillin selection A99 polyA repeat encoding mRNA vector pT3/T7 A99 pA (see Table 8); FIG. 4E) Pol I-dependent pUC origin-kanR selection A99 polyA repeat encoding mRNA vector NTC7-T7 A99 pA (see Table 8); and FIG. 4F) Pol III-dependent R6K origin-RNA-OUT antibiotic free selection A99 polyA repeat encoding mRNA vector NTC9-T7 A99 pA (see Table 8). The location of the A60 or A99 poly A repeat relative to the bacterial backbone replication origins and selection markers are shown.

EXAMPLES

The methods of the current technology are further illustrated by the following examples. These are provided by way of illustration and are not intended in any way to limit the scope of the disclosure.

Example 1: pUC, and R6K Replication Origin Plasmid Replication and Production pUC origin vector replication and production background: The vast majority of therapeutic plasmids use the pUC origin which is a high copy derivative of the pMB1 origin (closely related to the ColE1 origin). For pMB1 replication, plasmid DNA synthesis is unidirectional and does not require a plasmid borne initiator protein. The pUC origin is a copy up derivative of the pMB1 origin that deletes the accessory ROP (rom) protein and has an additional temperature sensitive mutation that destabilizes the RNAI/RNAII interaction. Shifting of a culture containing these origins from 30 to 42° C. leads to an increase in plasmid copy number. pUC plasmids can be produced in a multitude of E. coli cell lines.

RNA-OUT antibiotic free selectable marker background: Antibiotic-free selection is performed in E. coli strains containing phage lambda attachment site chromosomally integrated pcAH63-CAT RNA-IN-SacB (P5/6 6/6) as described in Williams, Supra, 2008. SacB (Bacillus subtilis levansucrase) is a counterselectable marker which is lethal to E. coli cells in the presence of sucrose. Translation of SacB from the RNA-IN-SacB transcript is inhibited by plasmid encoded RNA-OUT (FIG. 1B). This facilitates plasmid selection in the presence of sucrose, by inhibition of SacB mediated lethality.

R6K origin vector replication and production background: The R6K gamma plasmid replication origin requires a single plasmid replication protein π that binds as a replication initiating monomer to multiple repeated 'iteron' sites (seven core repeats containing TGAGNG consensus) and as a replication inhibiting dimer to repressive sites (TGAGNG) and to iterons with reduced affinity. Replication requires multiple host factors including IHF, DnaA, and primosomal assembly proteins DnaB, DnaC, DnaG (Abhyankar et al., 2003 J Biol Chem 278:45476-45484). The R6K core origin contains binding sites for DnaA and IHF that affect plasmid replication since π, IHF and DnaA interact to initiate replication.

Different versions of the R6K gamma replication origin have been utilized in various eukaryotic expression vectors, for example pCOR vectors (Soubrier et al., 1999, Gene Therapy 6:1482-88) and a CpG free version in pCpGfree vectors (Invivogen, San Diego CA), and pGM169 (University of Oxford). Incorporation of the R6K replication origin per se does not improve transgene expression levels compared to an optimized pUC origin vector (Soubrier et al., Supra, 1999). However, use of a conditional replication origin such as R6K gamma that requires a specialized cell line for propagation adds a safety margin since the vector will not replicate if transferred to a patient's endogenous flora.

A highly minimalized 6 iteron R6K gamma derived replication origin (SEQ ID NO:1; FIG. 1E) that contains core sequences required for replication (including the DnaA box and stb 1-3 sites; Wu et al., 1995. J Bacterial. 177: 6338-6345), but with the upstream π dimer repressor binding sites and downstream π promoter deleted (by removing one copy of the iterons) was described in Williams, Supra, 2014 and included herein by reference. This R6K origin contains 6 tandem direct repeat iterons (FIG. 1E). The NTC9385R Nanoplasmid™ vector including this minimalized R6K origin and the RNA-OUT AF selectable marker in the spacer region, was described in Williams, Supra, 2014 and included herein by reference.

Typical R6K production strains express from the genome the π protein derivative PIR116 that contains a P106L substitution that increases copy number (by reducing π dimerization; monomers activate while π dimers repress). Fermentation results with pCOR (Soubrier et al., Supra, 1999) and pCpG plasmids (Hebei H L, Cai Y. Davies L A, Hyde S C, Pringle I A, Gill D R. 2008. Mal Ther 16: S110) were low, around 100 mg/L in PIR116 cell lines.

Mutagenesis of the pir-116 replication protein and selection for increased copy number has been used to make new production strains. For example, the TEX2pir42 strain contains a combination of P106L and P42L. The P42L mutation interferes with DNA looping replication repression. The TEX2pir42 cell line improved copy number and fermentation yield with pCOR plasmids with reported yields of 205 mg/L (Soubrier F. 2004. World Patent Application WO2004033664).

Other combinations of π copy number mutants that improve copy number include 'P42L and P113S' and 'P42L, P106L and F107S' (Ahhvankar et al., 2004, J Biol Chem 279:6711-6719).

Williams, Supra, 2014 describes host strains expressing phage HK022 attachment site integrated pL promoter heat inducible π P42L, P106L and F107S high copy mutant replication (Rep) protein for selection and propagation of R6K origin Nanoplasmid™ vectors. This is an additional Nanoplasmid™ safety factor since R6K origin vectors can only replicate within the engineered Rep protein-expressing *E. coli* host strain.

RNA-OUT selectable marker-R6K plasmid propagation and fermentations described in Williams, *Supra,* 2014 were performed using heat inducible 'P42L, P106L and F107S' π copy number mutant cell lines such as DH5α host strain NTC711772=DH5α, dcm-att$_\lambda$::P$_{5/6}$ $_{6/6}$-RNA-IN-SacB, catR; att$_{HK022}$::pL (OL1-G to T) P42L-P106L-F107S (P3-), SpecR StrepR. Production yields up to 695 mg/L were reported.

Additional cell lines were created and disclosed herein including:

NTC821601 DH5α att$_\lambda$::P$_{5/6}$ $_{6/6}$-RNA-IN-SacB, catR; att$_{HK022}$::pL (OL1-G to T) P42L-P106L-F107S (P3-), SpecR StrepR=dem+version of NTC711772

NTC940211 DH5α att$_\lambda$::P$^{5/6}$ $^{6/6}$-RNA-IN-SacB, catR; att$_{HK022}$::pL (OL1-G to T) P42L-P106I-F107S P113S (P3-), SpecR StrepR=high copy substitution of P106I for P106L combined with P113S to create a quadruple copy number increasing mutant rep protein derivative of NIC821601

NTC1050811 DH5α, att$_\lambda$::P$_{5/6}$ $_{6/6}$-RNA-IN-SacB, catR; att$_{HK022}$::pL (OL1-G to T) P42L-P106I-F107S P113S (P3-), SpecR StrepR; att$_{\varphi80}$::pARA-CI857ts, tetR=pARA-CI857ts derivative of NTC940211. This strain contains a phage φ80 attachment site chromosomally integrated copy of a arabinose inducible CI857ts gene. Addition of arabinose to plates or media (e.g. to 0.2-0.4% final concentration) induces pARA mediated CI857ts repressor expression which reduces copy number at 30° C. through CI857ts mediated downregulation of the Rep protein expressing promoter [i.e. additional CI857ts mediates more effective downregulation of the pL (OL1-G to T) promoter at 30° C.]. Copy number induction after temperature shift to 37-42° C. is not impaired since the CI857ts repressor is inactivated at these elevated temperatures. A dcm-derivative (NTC1050811 dcm-) is used in cases where dcm methylation is undesirable.

NTC1011641; Stbl4 att$_\lambda$::P5/6 6/6-RNA-IN-SacB, catR; att$_{HK022}$::pL P42L-P106L-F107S (P3-) SpecR StrepR=Stbl4 version of NTC661135 (XL1 Blue-dcm-att$_\lambda$::P$_{5/6}$ $_{6/6}$-RNA-IN-SacB, catR; att$_{HK022}$::pR pL P42L-P106L-F107S (P3-) SpecR StrepR described in Williams, *Supra,* 2014

Nanoplasmid™ production yields are improved with the quadruple mutant heat inducible pL (OL1-G to T) P42L-P106I-F107S P113S (P3-) compared to the triple mutant heat inducible pL (OL1-G to T) P42L-P106L-F107S (P3-) described in Williams, *Supra,* 2014. Yields in excess of 2 g/L Nanoplasmid™ have been obtained with the quadruple mutant NTC1050811 cell line (e.g. 2240 mg/L with NTC9 T7 A99 pA, Table 8)

Use of a conditional replication origin such as these R6K origins that requires a specialized cell line for propagation adds a safety margin since the vector will not replicate if transferred to a patient's endogenous flora.

Example 2: pUC and R6K Origin Vector Production

Shake flask production: Shake flask production was performed using proprietary Plasmid+ shake culture medium. The seed cultures were started from glycerol stocks or colonies and streaked onto LB medium agar plates containing 50 µg/mL antibiotic (for ampR or kanR selection plasmids) or 6% sucrose Tor RNA-OUT selection plasmids). The plates were grown at 30-32° C.; cells were resuspended in media and used to provide approximately 2.5 OD$_{600}$ inoculums for the 500 mL Plasmid+ shake flasks that contained 50 µg/mL antibiotic for ampR or kanR selection plasmids or 0.5% sucrose to select for RNA-OUT plasmids. Flask were grown with shaking to saturation at the growth temperatures as indicated in Tables 5, 6, 7, and 9.

Fermentation production: Fermentations were performed using proprietary fed-batch media (NTC3019, HyperGRO media) in New Brunswick BioFlo 110 bioreactors as described (Carnes and Williams, *Supra,* 2011). The seed cultures were started from glycerol stocks or colonies and streaked onto LB medium agar plates containing 50 µg/mL antibiotic (for ampR or kanR selection plasmids) or 6% sucrose (for RNA-OUT selection plasmids). The plates were grown at 30-32° C.; cells were resuspended in media and used to provide approximately 0.1% inoculums for the fermentations that contained 50 µg/mL antibiotic for ampR or kanR selection plasmids or 0.5% sucrose for RNA-OUT plasmids. HyperGRO temperature shifts were as indicated in Tables 8 and 9.

Production hosts: pUC origin AmpR or KanR plasmid fermentations were performed in *E. coli* strain DH5α [F-Φ80lacZΔM15 Δ(lacZYA-argF) U169 recA1 endA1 hsdR17 (rK-, mK+) phoA supE44λ-thi-1 gyrA96 relA1] (Invitrogen, Carlsbad CA) or Stbl4.

Antibiotic-free pUC origin RNA-OUT plasmid fermentations were performed in *E. coli* strain DH5α containing phage lambda attachment site chromosomally integrated pCAH63-CAT RNA-IN-SacB (P5/6 6/6) as described in Williams, *Supra,* 2008. The production strain is NTC4862=DH5α attλ::P5/6 6/6-RNA-IN-SacB, catR.

Antibiotic-free R6K gamma origin RNA-OUT plasmid propagation and fermentations were performed using *E. coli* RNA-OUT selection hosts further encoding phage HK022 attachment site integrated pL promoter heat inducible π copy number mutant cell line lines, methods for the creation of which are described in Williams, *Supra,* 2014 and included herein by reference.

Production Strains:

pUC Origin-AmpR or KanR Antibiotic Selection Hosts
DH5α
Stbl4 pUC Origin-RNA-OUT Sucrose Selection Hosts
NTC4862 DH5α att$_\lambda$::P$_{5/6}$ $_{6/6}$-RNA-IN-SacB, catR
NTC1011592 Stbl4 attλ::P5/6 6/6-RNA-IN-SacB, catR R6K Origin-RNA-OUT Sucrose Selection Nanoplasmid™ hosts
NTC1050811 DH5α att$_\lambda$::P$_{5/6}$ $_{6/6}$-RNA-IN-SacB, catR; att$_{HK022}$::pL (OL1-G to T) P42L-P106I-F107S P113S (P3-), SpecR StrepR; att$_{\varphi80}$::pARA-CI857ts, tetR.
NTC1011641 Stbl4 attλ::P5/6 6/6-RNASacB, catR; att$_{HK022}$::pL P42L-P106L-F107S (P3-) SpecR StrepR Analytical Methods: Culture samples were taken at key points and at regular intervals during all fermentations, Samples were analyzed immediately for biomass (OD$_{600}$) and for plasmid yield. Plasmid yield was determined by quantification of plasmid obtained from Qiagen Spin Miniprep Kit preparations as described (Carries and Williams, *Supra,* 2011), Briefly, cells were alkaline lysed, clarified, plasmid was column purified, and eluted prior to quantification. Plasmid quality was determined by agarose gel electrophoresis analysis (AGE) and was performed on 0.8-1% Tris/acetate/EDTA (TAE) gels as described in Carnes and Williams, *Supra,* 2011.

Example 3: pUC and R6K Origin Structured Vector Construction and Manufacturing The R6K gamma origin (SEQ ID NO:1; FIG. 1E)-RNA-OUT (SEQ ID NO:5; FIG. 1B) bacterial replication-selection region (SEQ ID NO:8; FIG. 1C) was cloned into the polylinker region of a variety of pUC57 based vectors to create the pNTC-NP1, pNTC-NP2, pNTC-NP3, pNTC-NP4, pNTC-NP5, pNTC-NP6, pNTC-NP7, vectors. Each vector has different flanking restriction sites that can be used to retrofit a target vector to R6K replication-RNA-OUT selection. The 5' and 3' polylinker sequences flanking the R6K-RNA-OUT insert in the pNTC-NP 1-7 vectors are shown in Table 4. A pUC57 based version of the 1 CpG R6K gamma origin-2 CpG RNA-OUT bacterial replication-selection region (SEQ ID NO:9; FIG. 1D) was also created (pNTC-3xCpG NP1) and is shown in Table 4.

SEQ ID NO:18 7 iteron 3225 bp R6K origin vector: a biomass of 137 $OD_{600}$; plasmid titer of 1503 mg/L; plasmid specific yield of 11.0 mg plasmid/L/$OD_{600}$ The 7 iteron R6K gamma origin in SEQ ID NO:18 is a tandem duplication of iteron 5 (FIG. 1F; SEQ ID NO:18) but the 7 iteron R6K gamma origin vectors of the invention can be tandem duplications of any of the iterons given as SEQ ID NO:19; SEQ ID NO:20; SEQ ID NO:21; SEQ ID NO:22; SEQ ID NO:23 (FIG. 1E), or random combinations of SEQ ID NO:19; SEQ ID NO:20; SEQ ID NO:21; SEQ ID NO:22; SEQ ID NO:23 into 7 iteron R6K origin compositions, or iteron repeat variants that retain the TGAGNG consensus. Additional iteron derivatives (e.g. 8, 9 or 10 iteron vectors) are also contemplated for practice of the invention.

TABLE 4

| pNTC multiple cloning site flanked R6K Origin-RNA-OUT selection marker vectors | | | | | | |
|---|---|---|---|---|---|---|
| Vector | R6K 5' flanking restriction sites | trpA term | R6K origin | Linker site | RNA OUT Selection marker | RNA-OUT 3' flanking restriction site |
| pNTC-NP1 (SEQ ID NO: 10) | EcoRI, SacI, KpnI, NruI, NsiI, XmaIII, NotI, NheI | Yes | SEQ ID NO: 1 | DraIII[a] | SEQ ID NO: 5 | NheI BamHI, XmaI, ApaI, SalI, HincII, PstI, StuI, AatI, SphI, HindIII (in R6K) |
| pNTC-NP2 (SEQ ID NO: 11) | EcoRI, SacI, KpnI, NruI, NsiI, XmaIII, NotI, NheI | Yes | SEQ ID NO: 1 | DraIII[a] | SEQ ID NO: 5 | SpeI, XmaI, SspI BamHI, XmaI, ApaI, SalI, HincII, PstI, StuI, AatI, SphI, HindIII (in R6K) |
| pNTC-NP3 (SEQ ID NO: 12) | EcoRI, SacI, KpnI, NruI, NsiI, XmaIII, NotI, NheI | Yes | SEQ ID NO: 1 | DraIII[a] | SEQ ID NO: 5 | KpnI, SacI BamHI, XmaI, ApaI, SalI, HincII, PstI, StuI, AatI, SphI, HindIII (in R6K) |
| pNTC-NP4 (SEQ ID NO: 13) | NheI, XmaIII, NotI, NsiI, NruI, KpnI, SacI BamHI, XmaI, ApaI, SalI, HincII, SfcI, PstI, StuI, AatI, SphI, HindIII (in R6K) | Yes | SEQ ID NO: 1 | DraIII[a] | SEQ ID NO: 5 | EcoRI, SacI, KpnI |
| pNTC-NP5 (SEQ ID NO: 14) | KasI, NheI | Yes | SEQ ID NO: 1 | DraIII[a] | SEQ ID NO: 5 | KpnI AflIII PstI, AatI, SphI, HindIII (in R6K) |
| pNTC-NP6 (SEQ ID NO: 15) | EcoRI, PstI, EcoRV, BstXI, NotI, NheI | Yes | SEQ ID NO: 1 | DraIII[a] | SEQ ID NO: 5 | KpnI, ApaI, PvuI, SalI, SacI |
| pNTC-NP7 (SEQ ID NO: 16) | BssHII PacI NheI | Yes | SEQ ID NO: 1 | DraIII[a] | SEQ ID NO: 5 | KpnI PacI BssHII |
| pNTC-3x CpG NP1 (SEQ ID NO: 17) | XhoI, XbaI, ApaI, SalI, HincII, PstI, StuI, AatI, SphI, HindIII (in R6K) | No | SEQ ID NO: 2 | BsrGI | SEQ ID NO: 7 | EcoRI, SacI, KpnI, NruI, NsiI, XmaIII, NotI, NheI, KpnI |

[a]Non-palindromic unique 3 bp NNN sticky end DraIII site (CACNNNGTG) separating R6K and RNA-OUT of sequence CACGTTGTG can be used to assemble R6K and RNA-OUT from separate pNTC vectors in directional multi-fragment ligation reactions The R6K gamma origin (SEQ ID NO:1) is an engineered 6 iteron R6K origin (FIG. 1E). A pUC57 based version of a 7 iteron R6K gamma origin (SEQ ID NO:18; FIG. 1F)-RNA-OUT (SEQ ID NO:5; FIG. 1B) bacterial replication-selection region was also created and used to construct and evaluate the utility of additional iterons on manufacturing. Similarly, high quality, high yield manufacture was obtained with vectors differing only by containing either the SEQ ID NO:18 seven iteron R6K gamma origin or the six iteron R6K gamma origin (SEQ ID NO:1). For example, the following harvest production yields were obtained in 30-42° C. 10 hr ramp temperature shift HyperGRO fermentations:

SEQ ID NO:1 6 iteron 3203 bpR6K origin vector: a biomass of 120 $OD_{600}$; plasmid titer of 1363 mg/L; plasmid specific yield of 11.3 mg plasmid/L/$OD_{600}$ Viral and non-viral vector pUC origin-antibiotic selection bacterial backbone retrofits to R6K-RNA-OUT were performed by:

1) selecting restriction sites that flank the pUC origin and antibiotic selection marker region in the target viral and non-viral vector;
2) identifying a pNTC-NP compatible polylinker -R6K-RNA-OUT polylinker cassette (either pNTC-NP1, 2, 3, 4, 5, 6, or 7; Table 4);
3) Excising the pUC origin antibiotic selection marker region and replacing with the selected R6K origin RNA-OUT region using the selected restriction digestion approach and standard ligase mediated cloning.

In some cases, the R6K origin and RNA-OUT units were assembled in multi-fragment ligations from separate restriction fragments using the non-palindromic DraIII linker site (see Table 4). In the case of the fd6 Ad helper retrofit (Table 9), a 3-fragment ligation was performed using a short 500 bp synthetic gene DraIII RNA-OUT-Ad helper-AvrII to link RNA-OUT to a unique AvrII site in the fd6 Ad helper eukaryotic region in a 12 kb AvrII-SalI restriction fragment, and to a R6K origin-DraIII fragment from pNTC-NP4.

Example vector maps and vector characteristics of the original pUC origin-antibiotic selection marker vector and the retrofitted R6K origin-RNA-OUT antibiotic free selection marker vectors are shown for Sleeping Beauty (FIG. 2; Table 6), AAV (FIG., 3; Table 7) and mRNA (FIG. 4; Table 8) vectors. The vector characteristics of the original pUC origin-antibiotic selection marker vector and the retrofitted R6K origin-RNA-OUT antibiotic free selection marker vectors are shown for AAV helper vectors (Table 8). The vector characteristics of pUC origin-RNA-OUT antibiotic free selection marker vector and the retrofitted R6K origin-RNA-OUT antibiotic free selection marker vectors are shown for Lentiviral vectors (Table 5) and AAV vectors (Table 7).

In all cases, the bacterial backbone size was <1 kb in the R6K origin-RNA-OUT antibiotic free selection marker retrofitted vectors (460-610 bp). This is well below the 1.1 kb bacterial backbone size limit required to improve vector expression level (Tables 1-2) and duration (Quiviger et al., Supra, 2014). In all cases, the original pUC origin-antibiotic selection bacterial backbone prior to retrofit was >1.2 kb (2340-2750 bp) as were the pUC origin-RNA-OUT retrofits (1210-1500 bp). Thus, these AAV, AAV helper, Sleeping Beauty, and Lentiviral R6K origin-RNA-OUT antibiotic free selection marker retrofit vectors meet the short spacer region requirement for improved expression level and duration compared to the original pUC origin-antibiotic selection marker vector. Additionally, these AAV, AAV helper, Sleeping Beauty, and Lentiviral R6K origin-RNA-OUT antibiotic free selection marker retrofit vectors have no chance of antibiotic marker gene transfer by transduction (AAV, Lentiviral vectors) or transposition (Sleeping Beauty vectors) due to removal of the Kara or ampR antibiotic resistance selection marker in the parent vector. Additionally, the vectors of the current technology do not require the complicated difficult to scale expensive additional manufacturing steps required to remove the large bacterial region between the eukaryotic polyA and promoter with minicircle vectors (Kay et al., Supra, 2010).

However, in a Lentiviral vector the eukaryotic region contains flanking direct repeal LTRs, in an AAV vector the eukaryotic region contains flanking inverted terminal repeats, while in a Sleeping Beauty transposon vector the eukaryotic region contains flanking transposon IR/DR termini. These flanking sequences are all structured DNA sequences.

Levy, Supra, 2004 teaches that replication intermediates form when any high copy number prokaryotic origin of replication is <1 kb from a structured DNA sequence such as an enhancer, LTR or IRES, but not when the high copy replication origin is >1.5 kb. Consistent with this, Replication intermediates were formed in all pUC origin-RNA-OUT marker vectors in which the pUC origin was <1 kb from a Lentiviral vector LTR (Table 5: 400 bp) or a pUC origin-antibiotic resistance marker vector in which the pUC origin was <1 kb from a Sleeping Beauty IR/DR (Table 6; 280 bp). For AAV and mRNA vectors, the original pUC origin-antibiotic selection marker vectors have the pUC origin 0 bp from an ITR (AAV vector; Table 7) or 170 bp from a A99 repeat (mRNA vector, Table 8) which may make a replication intermediate that is too small to detect on an agarose gel. However, in these cases production yields were very low, indicative of low plasmid copy number due to replication blockage. By contrast, as expected, in the case where the original pUC origin-antibiotic selection marker vector pUC origin was >1.5 kb from a structured DNA sequence (A60 repeat), high plasmid production yields were obtained (Table 8: snRNA vector pGEM4Z T7 A60).

Williams, Supra, 2017 reported that pUC origin vector production yield is improved with a PAS-BH extended pUC origin when the pUC origin is >1.5 kb from a homopolymeric A64C31 repeat. However, production yields were low when a PAS-BH extended pUC origin is orientated <400 bp from the A64C31 repeat (Table 8, see footnotes d and e). This teaches that addition of a PAS-BH primosomal assembly site does not overcome the poor pUC origin directed replication of closely positioned structured DNA sequences.

Since the pUC origin itself is 1 kb, there is no configuration to make a <1.1 kb bacterial region AAV, Lentiviral, Retroviral or transposon vector containing the pUC origin which is not predicted to produce replication intermediates as seen above and predicted by Levy, Supra, 2004 and poor plasmid yields as reported herein.

Surprisingly, replication intermediates were not observed in any R6K origin-RNA-OUT antibiotic free selection marker retrofitted vectors, include those in which the R6K origin was <1 kb from a Lentiviral vector LTR (Table 5: 400 bp) or a Sleeping Beauty IR/DR (Table 6; <40 bp). Further, for AAV vectors, while the original pUC origin-antibiotic selection marker vectors with the pUC origin 0 bp from the ITR had very poor production yields, the two R6K origin-RNA-OUT antibiotic free selection marker retrofitted vectors with the R6K origin 40 bp from the ITR had much higher production yields (Table 7). This improved production is specific to R6K and not RNA-OUT, since the two AAV pUC-RNA-OUT retrofits with the pUC origin 50 bp from the ITR had equally poor plasmid production yields as the original pUC antibiotic marker vector (Table 7); as well the direct comparison of pUC-RNA-OUT with R6K-RNA-OUT retrofits positioned 400 bp from an LTR repeat in a Lentiviral backbone showed replication intermediates with all three pUC-RNA-OUT backbones but none of the three R6K-RNA-OUT backbones (Table 5), This surprising improvement in plasmid copy number (plasmid production yields) and quality (eliminated replication intermediates) with the R6K origin vector implies that the R6K origin can replicate through a structured DNA sequence more effectively than the pUC origin. While Levy, Supra, 2004 teaches that replication intermediates form when any high copy number prokaryotic origin of replication is <1 kb from a structured DNA sequence such as an enhancer, LTR or IRES, but not when the high copy replication origin is >1.5 kb away, the examples provided by Levy, Supra, 2004 were all with pUC origin plasmids.

A fundamental difference between these replication origins is that the pUC origin is a Pol I dependent origin of replication while the R6K origin is a Pol III dependent origin of replication. With the pUC origin the RNAII primer forms an RNA: DNA R-loop that is cleaved by RNase H to create a primer for DNA Pol I directed DNA synthesis during initial leading strand synthesis. DNA synthesis then converts from slow DNA Pol I to the highly processive DNA Pol III from 400 bp to up to 1.3 kb downstream of the origin (Allen et al., 2011. Nucleic Acids Research 39:7020-33). The R6K gamma replication origin rep protein interacts with dnaB helicase and dnaG primase which creates short RNA primers for DNA Pol III replication without requirement for DNA Pol I (Abhyankar et al., Supra. 2003). The pUC origin DNA Pol I replication zone of up to 1.3 kb from the origin corresponds closely with the Levy, *Supra,* 2004 defined upper limit of replication intermediate formation (between 1 and 1.5 kb from the origin). We propose that the observed surprisingly improved replication of structured DNA when in close proximity to the R6K but not the pUC origin is due to an unexpected improvement of replication of structured DNA sequences by DNA Pol III compared to DNA Pol I.

The vector methods and compositions disclosed herein demonstrate that a Pol III-dependent origin of replication such as the R6K origin can be used to replicate structured DNA sequences which are poorly replicated by a Pol I-dependent origin of replication such as the pUC origin.

These results demonstrate the vectors of the invention are useful for improving viral and non-viral vector manufacturing yield and quality.

Example 4: Improved Performance of R6K Origin Structured Vector

The vectors of the invention are additionally useful for eliminating antibiotic resistance marker gene transfer by viral and non-viral vectors; reducing transfection associated toxicity; improving transposition from non-viral transposon vectors; improving packaging titers from viral vectors; improving expression of viral and non-viral vector encoded transgenes, etc.

As an example, R6K origin third generation lentiviral vectors [4 vectors: Table 5 transfer plasmid, gag pol packaging plasmid; env plasmid; REV plasmid (not shown) with R6K origin and <1 kb bacterial backbone] of the invention showed reduced toxicity and improved viral packaging titers compared to pUC origin vector comparators with >1.5 kb bacterial backbone. Transfection of Lenti-X 293 T cell line (Takara Bio Mountain View, CA) with Table 5 R6K origin third generation lentiviral vectors with <1 kb bacterial backbone or original pUC origin-antibiotic selection marker vector with >1.5 kb bacterial backbone control in 24 well plates using Lipofectamine 3000 (Thermo Fisher Scientific, Waltham, MA) as recommended by the manufacturer resulted in higher titer lentivirus production (>1.5 kb bacterial backbone pUC origin control vectors: 1.00x±0.32; <1 kb bacterial backbone R6K origin vectors 1.45x±0.42) as measured using the Lenti-X p24 Rapid Titer Kit (Takara Bio Mountain View, CA). Transfection of Lenti-X 293 T cell line in 24 well plates with Table 5 third generation lentiviral vectors (>1.5 kb bacterial backbone pUC origin control or <1 kb bacterial backbone R6K origin) using Calcium Phosphate transfection as described (Marino M P, Luce M J, Reiser J. 2003, *Methods Mol Biol* 229:43-55) resulted in higher titer lentivirus production (>1.5 kb bacterial backbone pUC origin control: 1.00x±0.30; <1 kb bacterial backbone R6K origin vectors: 1.32x±0.19) as measured using the Lenti-X p24 Rapid Titer Kit (Takara Bio Mountain View, CA). Significantly, Calcium Phosphate transfection of the >1.5 kb bacterial backbone pUC origin third generation Lentiviral vectors resulted in extensive transfection associated toxicity (>80% cell death) compared to low toxicity with the R6K origin <1 kb bacterial backbone R6K origin third generation Lentiviral vectors in this 24 well plate transfection. This reduced transfection associated toxicity should result in dramatically improved viral titers in larger manufacturing scale transfections. These results demonstrate the <1 kb bacterial backbone R6K origin Nanoplasmid vectors of the invention reduce transfection associated toxicity and improve packaging titers from viral vectors compared to >1.5 kb bacterial backbone vectors.

SUMMARY

While the above description contains many examples, these should not be construed as limitations on the scope of the disclosure, but rather should be viewed as an exemplification of preferred embodiments thereof. Many other variations are possible.

For example, in the vectors of the current technology various orientations of the Pol III dependent replication origin, and the RNA selectable marker, may be utilized. For example, any of the eight orientations of the Pol III dependent replication origin, and the RNA selectable marker in vectors of the current technology may be used (i.e. ←Pol III replication origin RSM→; ←Pol III replication origin←RSM; Pol III replication origin→RSM→; Pol III replication origin→←RSM; ←RSM Pol III replication origin→; ←RSM←Pol III replication origin; RSM→Pol III replication origin→; RSM→←Pol III replication origin).

Further, a variety of RNA selectable markers know in the art may be substituted for RNA-OUT.

Further, an antibiotic resistance maker may be substituted for RNA-OUT, for example in the case where a simple retrofit of the pUC origin to the R6K origin is desired to improve plasmid production yield and or quality.

Thus, the reader will see that the improved Pol III dependent replication origin vectors of the current technology provide for an approach to reduce transfection associated toxicity, improve transposition from non-viral transposon vectors, improve packaging titers from viral vectors, improve expression of viral and non-viral vector encoded genes, and eliminate viral vector and non-viral vector mediated antibiotic selection marker gene transfer (i.e. through incorporation of a bacterial region preferably less than 1000 bp) while dramatically improving manufacture compared to alterative vectors such as pUC plasmids and minicircles.

Accordingly, the scope of the disclosure should be determined not by the embodiments illustrated, but by the appended claims.

TABLE 5

| Lentiviral vectors: pUC origin-RNA-OUT versus R6K origin-RNA-OUT shake flask production yields/quality | | | | | | | | | | | |
|---|---|---|---|---|---|---|---|---|---|---|---|
| Lentiviral Vector | Replication origin | Vector size | Transfer plasmid bacterial backbone (LTR spacing)[a] | Replication origin spacing from SV40 Ori[b] | Replication origin spacing front LTR[c] | Cell line[d] | Production culture[e] | Harvest OD$_{600}$ | Harvest spec yield (mg/L/ OD$_{600}$) | Harvest yield (mg/L) | Production quality[f] |
| Transfer plasmid 1 with SV40 Ori | pUC origin | 9.9 kb | 1210 bp (1210 bp) | <50 bp | 400 bp | DH5α | 30 to 37 C. | 7.5 | 3.4 | 26 | CCC Monomer + Replicate Intermediate |

TABLE 5-continued

Lentiviral vectors: pUC origin-RNA-OUT versus R6K origin-RNA-OUT shake flask production yields/quality

| Lentiviral Vector | Replication origin | Vector size | Transfer plasmid bacterial backbone (LTR spacing)[a] | Replication origin spacing from SV40 Ori[b] | Replication origin spacing front LTR[c] | Cell line[d] | Production culture[e] | Harvest OD$_{600}$ | Harvest spec yield (mg/L/ OD$_{600}$) | Harvest yield (mg/L) | Production quality[f] |
|---|---|---|---|---|---|---|---|---|---|---|---|
| | R6K origin | 9.2 kb | 460 bp (460 bp) | <50 bp | 400 bp | DH5α | 30 to 37 C. | 5.0 | 4.7 | 24 | CCC Monomer |
| Transfer plasmid 2 with SV40 Ori | pUC origin | 7.3 kb | 1210 bp (1210 bp) | <50 bp | 400 bp | DH5α | 30 to 37 C. | 9.0 | 3.9 | 35 | CCC Monomer + Replicate Intermediate |
| | R6K origin | 6.5 kb | 460 bp (460 bp) | <50 bp | 400 bp | DH5α | 30 to 37 C. | 8.4 | 7.2 | 61 | CCC Monomer |
| Transfer plasmid 3 with SV40 Ori | pUC origin | 8.3 kb | 1210 bp (1210 bp) | <50 bp | 400 bp | DH5α | 30 to 37 C. | 16.8 | 3.0 | 51 | CCC Monomer + Replicate Intermediate |
| | R6K origin | 7.5 kb | 460 bp (460 bp) | <50 bp | 400 bp | DH5α | 30 to 37 C. | 11.9 | 7.7 | 92 | CCC Monomer |
| Gag pol packaging plasmid | pUC origin | 8.4 kb | 1210 bp | NA | NA | DH5α | 30 to 37 C. | 10.2 | 4.3 | 44 | CCC Monomer |
| | R6K origin | 7.5 kb | 460 bp | NA | NA | DH5α | 30 to 37 C. | 9.7 | 7.6 | 73 | CCC Monomer |
| Envelope plasmid | pUC origin | 5.4 kb | 1210 bp | NA | NA | DH5α | 30 to 37 C. | 17.0 | 5.7 | 96 | CCC Monomer |
| | R6K origin | 4.4 kb | 460 bp | NA | NA | DH5α | 30 to 37 C. | 10.8 | 6.0 | 65 | CCC Monomer |

[a]All vectors are antibiotic free RNA-OUT selection retrofits. Original pUC origin-antibiotic selection marker vector bacterial backbone size were all >1.5 kb
[b]Distance in bp from 3' end of replication origin to SV40 origin in direction of replication
[c]Distance in bp from 3' end of replication origin to nearest LTR in direction of replication
[d]DH5α = NTC4862 for pUC origin, NTC1050811 for R6K origin
[e]500 mL Plasmid + Shake Flask Culture temperature shifted from 30 to 37 C.
[f]Harvest plasmid preparations with detectable replication intermediates indicated. Levy, *Supra*, 2004 teach that replication intermediates form when any high copy number prokaryotic origin of replication is less than 1000 bp from a promoter/enhancer or LTR promoter or DNA repeat or a complex secondary structure such as an IRES, while replication intermediates do not form if the origin of replication is a distance greater than about 1.5 kb.

TABLE 6

Sleeping Beauty Transposon and transposase vector: pUC versus R6K origin shake flask production yields/quality

| Replication origin/ vector | Bacterial selection | Vector IR/DR Configuration | Vector size | bacterial backbone size (IR/DR spacing) | Replication origin spacing from IR/DR[a] | Cell line[b] | Production culture[c] | Harvest OD$_{600}$ | Harvest spec yield (mg/L/ OD$_{600}$) | Harvest yield (mg/L) | Production quality[d] |
|---|---|---|---|---|---|---|---|---|---|---|---|
| Transposon vector pUC origin (pUC57-kan-SB1: see FIG. 2) | KanR | IR DR(R) <pUC<kanR IR DR(L) Promoter> Transgene> | 5.5 kb | 2600 bp (2600 bp) | 280 bp | DH5α | 30 to 37 C. | 1.9 | 2.1 | 4 | CCC Monomer + Replicate Intermediate |
| Transposon vector R6K origin (NTC9-SB1: see FIG. 2) | RNA-OUT AF | IR DR(R) < R6K R-OUT > IR DR(L) Promoter> Transgene> | 3.4 kb | 475 bp (475 bp) | <40 bp | DH5α | 30 to 37 C. | 11.2 | 1.0 | 11 | CCC Monomer |
| Transposon vector R6K origin (NTC9-SB2) | RNA-OUT AF | IR DR(R) < R6K R-OUT > IR DR(L) Promoter> Transgene> | 3.6 kb | 475 bp (475 bp) | <40 bp | DH5α | 30 to 37 C. | 4.1 | 6.2 | 25 | CCC Monomer |
| Transposase vector pUC origin | KanR | Not Applicable | 4.7 kb | 2600 bp (NA) | Not Applicable | DH5α | 30 to 37 C. | 21.6 | 1.8 | 39 | CCC Monomer |

TABLE 6-continued

Sleeping Beauty Transposon and transposase vector: pUC versus R6K origin shake flask production yields/quality

| Replication origin/ vector | Bacterial selection | Vector IR/DR Configuration | Vector size | bacterial backbone size (IR/DR spacing) | Replication origin spacing from IR/DR[a] | Cell line[b] | Production culture[c] | Harvest OD600 | Harvest spec yield (mg/L/ OD600) | Harvest yield (mg/L) | Production quality[d] |
|---|---|---|---|---|---|---|---|---|---|---|---|
| Transposase vector R6K origin | RNA-OUT AF | Not Applicable | 2.5 kb | 475 bp (NA) | Not Applicable | DH5α | 30 to 37 C. | 10.9 | 4.7 | 51 | CCC Monomer |

[a]Distance in bp from 3' end of replication origin to nearest Sleeping Beauty IR/DR in direction of replication
[b]DH5α = DH5α for pUC57-kanR pUC origin, NTC1050811 for R6K origin
[c]500 mL Plasmid + Shake Flask Culture temperature shifted from 30 to 37 C.
[d]Harvest plasmid preparations with detectable replication intermediates indicated. Levy, *Supra*, 2004 teach that replication intermediates form when any high copy number prokaryotic origin of replication is less than 1000 bp from a promoter/enhancer or LTR promoter or DNA repeat or a complex secondary structure such as an IRES, while replication intermediates do not form if the origin of replication is a distance greater than about 1.5 kb.

TABLE 7

AAV vectors: pUC versus R6K origin shake flask production yields/quality

| AAV Vector | Replication origin | Bacterial selection | Vector Configuration | Vector size | bacterial backbone size (ITR spacing)[e] | Bacterial selection | Replication origin spacing from ITR[a] | Cell line[b] | Production culture[c] | Harvest OD600 | Harvest spec yield (mg/L/ OD600) | Harvest yield (mg/L) | Production quality[d] |
|---|---|---|---|---|---|---|---|---|---|---|---|---|---|
| Backbone 1[e] | pUC origin (pAAV: see FIG. 3) | AmpR | ITR <F1Ori-AmpR>pUC> ITR CMV-transgene-pA | 5.4 kb | 2600 bp (2600 bp) | AmpR | 0 bp | Stbl4 | 30-37 C. shake | 17.8 | 0.4 | 8 | CCC Monomer |
| | pUC origin (NTC8-AAV: see FIG. 3) | RNA-OUT AF | ITR <pUC R-OUT> ITR CMV-transgene-pA | 4.0 kb | 1240 bp (1240 bp) | RNA-OUT AF | 50 bp | Stbl4 | 30-37 C. shake | 10.4 | 0.7 | 7 | CCC Monomer |
| | R6K origin (NTC9-AAV: see FIG. 3) | RNA-OUT AF | ITR <R6K R-OUT> ITR CMV-transgene-pA | 3.3 kb | 490 bp (490 bp) | RNA-OUT AF | 40 bp | Stbl4 | 30-37 C. shake | 11.8 | 3.5 | 42 | CCC Monomer |
| | R6K origin | RNA-OUT AF | ITR <R6K R-OUT> Rep> Cap> ITR CMV-transgene-pA | 7.7 kb | 490 bp (4940 bp) | RNA-OUT AF | 40 bp | Stbl4 | 30-37 C. shake | 11.0 | 2.1 | 23 | CCC Monomer |
| Backbone 2 | pUC origin (NTC8) | RNA-OUT AF | ITR <pUC R-OUT> ITR CAG-transgene-WPRE-pA | 5.5 kb | 1250 bp (NA) | RNA-OUT AF | 50 bp | Stbl4 | 30-37 C. shake | 11.7 | 0.4 | 5 | CCC Monomer |
| | R6K origin (NTC9) | RNA-OUT AF | ITR <R6K R-OUT> ITR CAG-transgene-WPRE-pA | 4.8 kb | 490 bp (NA) | RNA-OUT AF | 40 bp | Stbl4 | 30-37 C. shake | 11.1 | 1.6 | 18 | CCC Monomer |

[a] Distance in bp from 3' end of replication origin from nearest AAV ITR in direction of replication

[b]Stbl4 = Stbl4 for pUC origin-ampR, NTC1011592 for pUC origin-RNA-OUT, NTC1011641 for R6K origin-RNA-OUT

[c]Plasmid + Shake Flask Culture temperature shifted from 30 to 37 C.

[d]High quality CCC monomer with no detectable replication intermediate and low amounts of recombination mediated ITR deletion. May not see replication intermediates on gel with pUC origin since <50 from DNA structure, but probably formed since plasmid yield lower than R6K origin

[e]A R6K origin-RNA-OUT MIP intron version of this vector with 6 bp ITR spacing was unclonable, presumably due to toxicity of juxtaposing the 2 AAV ITR immediately adjacent to each other. A R6K origin-RNA-OUT MIP intron version in a second AAV vector backbone (10 bp ITR spacing) was also unclonable

TABLE 8 mRNA vector: pUC versus R6K origin DH5α[f] HyperGRO[g] Fermentation Yields/quality

| polyA mRNA expression vector | Replication origin | Selection | Vector Configuration | Vector size | Bacterial backbone size | Replication origin bp from polyA | Harvest OD600 | Harvest spec yield (mg/L/OD600) | Harvest spec yield (mg/gWCW) | Harvest yield (mg/L) | Harvest yield (g)[b] | Production quality |
|---|---|---|---|---|---|---|---|---|---|---|---|---|
| pT3/T7 A99 pA[b] mRNA expression vector and retrofit derivatives | pUC origin (pT3/T7 A99 pA) | AmpR | A99<pUC< AmpR T7> Transgene | 7.2 kb | 2660 bp | 170 bp | 113 | 3.8 | 1.6 | 430[a] | 43 | CCC Monomer[i] |
| | pUC origin + PAS-BH[d] (NTC7 T7 A99 pA) | kanR | A99<KanR pUC>PAS-BH> T7> Transgene | 7.2 kb | 2660 bp | 5000 bp | 140 | 8.9 | 4.1 | 1250[a] | 12.5 | CCC Monomer |
| | R6K origin (NTC9 T7 A99 pA) | RNA-OUT AF | A99<R-OUT R6K> T7> Transgene | 5.2 kb | 610 bp | 4600 bp | 147 | 15.3 | 6.7 | 2240[a] | 22.4 | CCC Monomer |
| pGEM4Z A60 pA[c] mRNA expression vector and retrofit derivatives | pUC origin (pGEM4Z T7 A60 pA) | AmpR | A60 AmpR> pUC> T7> Transgene | 6.8 kb | 2500 bp | 4400 bp | 112 | 8.3 | 4.4 | 929 | 9.3 | CCC Monomer |
| | pUC origin + PAS-BH[e] (NTC8 T7 A60 pA) | RNA-OUT AF | A60<R-OUT pUC> PAS-BH> T7> Transgene | 5.9 kb | 1500 bp | 4600 bp | 146 | 11.5 | 4.9 | 1673[a] | 16.7 | CCC Monomer |
| | R6K origin (NTC9 T7 A60 pA) | RNA-OUT AF | A60<R-OUT R6K> T7> Transgene | 4.9 kb | 460 bP | 4300 bp | 113 | 13.1 | 5.0 | 1483[a] | 14.8 | CCC Monomer |

[a]PolyA region correct by sequencing

[b]gram plasmid/10 L fermentor

[c]See FIG. 4 for vector maps

[d]KanR-pUC + PASBH vector backbone described in Williams 2017 WO2017025447. This pUC + PASBH backbone dramatically improved plasmid yield when oriented >1.5 kb away from polyA64-polyC31 compared to a pUC origin oriented <200 bp away from the polyA64-polyC31 repeat or a pUC + PASBH origin oriented <400 bp away from the polyA64-polyC31 repeat (Williams, *Supra*, 2017, P1140-K2 versus P1140 and P1140-K1, Table 1). Thus PAS-BH does not dramatically improve pUC origin replication into a repeat structure <400 bp from the pUC origin.

[e]RNA-OUT-pUC + PASBH vector backbone described in Williams, *Supra*, 2017. This pUC + PASBH backbone dramatically improved plasmid yield when oriented >1.5 kb away from polyA64-polyC31 compared to a pUC origin oriented <200 bp away from the polyA64-polyC31 repeat or a pUC + PASBH origin oriented <400 bp away from the polyA64-polyC31 repeat. (Williams, *Supra*, 2017, Table 1: P1140-AF2 versus P1140 and P1140-AF1). Thus PAS-BH does not dramatically improve pUC origin replication into a repeat structure <400 bp from the pUC origin.

[f]DH5α = NTC4862 for NTC8; NTC1050811 for NTC9: NTC1050811 DH5α att$_\lambda$::P$_{5/6 \ 6/6}$-RNA-IN-SacB, catR; att$_{HK022}$::pL (OL1-G to T) P42L-P106I-F107S P113S (P3−), SpecR StrepR; att$_{\varphi80}$::pARA-CI857ts, TetR. Arabinose induces pARA-CI857ts expression which reduces copy number through CI857ts mediated downregulation of the Rep protein expressing pL promoter

[g]HyperGRO fermentation 30-42° C. temperature shift at 55 OD600. For NTC9 vectors fermentation media contained 0.2% arabinose

[h]Elango et al., 2005. *Biochemical and Biophysical Research Communications* 330: 958-66 teach polyA100 mRNA vectors are unstable in DH5α and XL1Blue and cannot be produced in mg quantities. See FIG. 4 for vector maps

[i]May not see replication intermediates on gel with pUC origin since <170 bp from DNA structure, but probably formed since plasmid yield lower than with R6K origin vectors

TABLE 9

AAV helper vectors: pUC versus R6K origin plasmid production yields/quality

| AAV Helper Vector | Replication origin | Selection | Vector size | bacterial backbone size | Cell line[b] | Production culture[a] | Harvest OD600 | Harvest spec yield (mg/L/OD600) | Harvest yield (mg/L) | Production quality |
|---|---|---|---|---|---|---|---|---|---|---|
| AAV2 Rep/AAV9 Cap (Rep Cap helper) | pUC origin | RNA-OUT AF | 5.7 kb | 1220 bp | DH5α | 30 to 37 C.[a] | 16.5 | 2.6 | 43 | CCC Monomer |
| | R6K origin | RNA-OUT AF | 4.9 kb | 470 bp | DH5α | 30 to 37 C.[a] | 17.5 | 5.5 | 96 | CCC Monomer |
| Fd6 (Ad Helper) | pUC origin | ampR | 15.4 kb | 2750 bp | Stbl4[c] | 30 C.[a,c] | 20 | 0.8[d] | 16[d] | CCC Monomer and deletion productions |
| | R6K origin | RNA-OUT AF | 12.9 kb | 540 bp | DH5α | 30 to 37 C.[a] | 17.8 | 1.3 | 23 | CCC Monomer |
| pHelper Rep Cap NP (Ad Helper + Rep Cap single helper plasmid) | R6K origin | RNA-OUT AF | 14.2 kb | 470 bp | DH5α | 30 to 37 C.[a] | 6.8 | 4.8 | 33 | CCC Monomer |
| pHelper (Ad Helper) | pUC origin | ampR | 11.6 kb | 2340 bp | DH5α | 30-42 C. HyperGRO shift | 129 | 14.2 | 1833 | CCC Monomer |

TABLE 9-continued

| AAV helper vectors: pUC versus R6K origin plasmid production yields/quality | | | | | | | | | | |
|---|---|---|---|---|---|---|---|---|---|---|
| AAV Helper Vector | Replication origin | Selection | Vector size | bacterial backbone size | Cell line[b] | Production culture [a] | Harvest OD$_{600}$ | Harvest spec yield (mg/L/ OD$_{600}$) | Harvest yield (mg/L) | Production quality |
| pHelper-NP (Ad Helper) | R6K origin | RNA-OUT AF | 9.8 kb | 460 bp | DH5α | 30-42 C. HyperGRO RAMP[e] | 84.5 | 18.1 | 1530 | CCC Monomer |

[a]500 mL Plasmid + Shake Flask Culture;

[b]DH5α = NTC1050811 for NTC9: NTC1050811 DH5α att$_λ$::P$_{5/6\ 6/6}$-RNA-IN-SacB, catR; att$_{HK022}$::pL (OL1-G to T) P42L-P106I-F107S P113S (P3−), SpecR StrepR; att$_{φ80}$::pARA-CI857ts, TetR. Arabinose induces pARA-CI857ts expression which reduces copy number through CI857ts mediated downregulation of the Rep protein expressing pL promoter. Retrofits were obtained using Sucrose + 0.2% Arabinose plates to reduce copy number

[c]Fd6 Stbl4 best cell line, Fd6/Stbl3 see deletions, Fd6/DH5α and Fd6/XL1Blue cell lines are unstable, used 30 C. throughout since plasmid lost in 30-37 C. process

[d]Actual yield lower due to high gDNA in minipreps

[e]HyperGRO fermentation, inoculated from sucrose + 0.2% arabinose culture grown at 30° C., arabinose added to batch medium to 0.2% final concentration. 30-42° C. ramp temperature shift

What is claimed is:

1. A method for replicating a covalently closed circular plasmid comprising the following steps:

a. providing a cell containing a covalently closed circular plasmid, the covalently closed circular plasmid comprising:

i. a backbone comprising a Pol III-dependent R6K origin of replication and an RNA-OUT RNA selectable marker, wherein the backbone is less than 1000 bp, and ii. an insert comprising a structured DNA sequence selected from the group consisting of an inverted repeat sequence, a direct repeat sequence, and a eukaryotic origin of replication, wherein the structured DNA sequence is located at a distance of less than 1000 bp from the Pol III-dependent R6K origin of replication in the direction of replication; and b. subjecting the cell to a fermentation process.

2. The method of claim 1, wherein the cell is an engineered Rep protein-expressing *E. coli* strain.

3. The method of claim 2, wherein the cell comprises a chromosomally-integrated arabinose inducible CI857ts gene.

4. The method of claim 3, wherein Rep protein includes the following mutations: P42L; P106I; F107S; and P113S.

5. The method of claim 1, wherein the insert is a transposon vector.

6. The method of claim 5, wherein the transposon vector comprises an inverted repeat sequence, or a direct repeat sequence.

7. The method of claim 1, wherein the insert is a transposase vector.

8. The method of claim 1, wherein the insert is a viral vector and the viral vector is an AAV vector.

9. The method of claim 8, wherein the AAV vector comprises an inverted repeat sequence.

10. The method of claim 1, wherein the insert is a viral vector and the viral vector is a lentiviral vector.

11. The method of claim 10, wherein the lentiviral vector comprises a direct repeat sequence or a eukaryotic origin of replication.

12. The method of claim 1, wherein the Pol III-dependent R6K origin of replication possesses at least 95% sequence identity to a sequence selected from the group consisting of SEQ ID NO: 1, SEQ ID NO: 2, SEQ ID NO: 3, SEQ ID NO: 4, and SEQ ID NO: 18.

13. The method of claim 1, wherein the RNA-OUT RNA selectable marker is an RNA-IN regulating RNA-OUT functional variant with at least 95% sequence identity to a sequence selected from the group consisting of SEQ ID NO: 5, and SEQ ID NO: 7.

14. The method of claim 1, wherein the structured DNA sequence is selected from the group consisting of a SV40 origin of replication, a viral LTR, a Lentiviral LTR, a Retroviral LTR, a transposon IR/DR repeat, a Sleeping Beauty transposon IR/DR repeat, and an AAV ITR.

15. The method of claim 1, wherein the fermentation process comprises growing the cells in media containing arabinose.

16. The method of claim 1, wherein the cell is an engineered Rep protein-expressing *E. coli* strain and comprises a chromosomally-integrated arabinose inducible CI857ts gene, wherein the structured DNA sequence is selected from the group consisting of a SV40 origin of replication, a viral LTR, a Lentiviral LTR, a Retroviral LTR, a transposon IR/DR repeat, a Sleeping Beauty transposon IR/DR repeat, and an AAV ITR, wherein the Pol III-dependent R6K origin of replication possesses at least 95% sequence identity to a sequence selected from the group consisting of SEQ ID NO: 1, SEQ ID NO: 2, SEQ ID NO: 3, SEQ ID NO: 4, and SEQ ID NO: 18, wherein the RNA-OUT RNA selectable marker is an RNA-IN regulating RNA-OUT functional variant with at least 95% sequence identity to a sequence selected from the group consisting of SEQ ID NO: 5, and SEQ ID NO: 7.

17. The method of claim 16, wherein the yield of the covalently closed circular plasmid following the fermentation process is in excess of 0.5 g/L.

18. A covalently closed circular plasmid comprising a backbone and an insert, the backbone comprising a Pol III-dependent R6K origin of replication and an RNA-OUT RNA selectable marker, wherein the backbone is less than 1000 bp, and the insert comprises a structured DNA sequence selected from the group consisting of an inverted repeat sequence, a direct repeat sequence, and a eukaryotic origin of replication, wherein the structured DNA sequence is located at a distance of less than 1000 bp from the Pol III-dependent R6K origin of replication in the direction of replication.

19. The covalently closed circular plasmid of claim 18, wherein the Pol III-dependent R6K origin of replication possesses at least 95% sequence identity to a sequence selected from the group consisting of SEQ ID NO: 1, SEQ ID NO: 2, SEQ ID NO: 3, SEQ ID NO: 4, and SEQ ID NO: 18.

20. The covalently closed circular plasmid of claim 18, wherein the RNA-OUT RNA selectable marker is an RNA-IN regulating RNA-OUT functional variant with at least 95% sequence identity to a sequence selected from the group consisting of SEQ ID NO: 5, and SEQ ID NO: 7.

21. The covalently closed circular plasmid of claim 18, wherein the structured DNA sequence is selected from the group consisting of a SV40 origin of replication, a viral LTR, a Lentiviral LTR, a Retroviral LTR, a transposon IR/DR repeat, a Sleeping Beauty transposon IR/DR repeat, and an AAV ITR.

22. The covalently closed circular plasmid of claim 18, wherein the insert is a transposon vector.

23. The covalently closed circular plasmid of claim 22, wherein the transposon vector comprises an inverted repeat sequence, or a direct repeat sequence.

24. The covalently closed circular plasmid of claim 18, wherein the insert is a transposase vector.

25. The covalently closed circular plasmid of claim 18, wherein the insert is a viral vector and the viral vector is an AAV vector.

26. The covalently closed circular plasmid of claim 25, wherein the AAV vector comprises an inverted repeat sequence.

27. The covalently closed circular plasmid of claim 18, wherein the insert is a viral vector and the viral vector is a lentiviral vector.

28. The covalently closed circular plasmid of claim 27, wherein the lentiviral vector comprises a direct repeat sequence or a eukaryotic origin of replication.

29. The covalently closed circular plasmid of claim 18, wherein the Pol III-dependent R6K origin of replication possesses at least 95% sequence identity to a sequence selected from the group consisting of SEQ ID NO: 1, SEQ ID NO: 2, SEQ ID NO: 3, SEQ ID NO: 4, and SEQ ID NO: 18, and wherein the RNA-OUT RNA selectable marker is an RNA-IN regulating RNA-OUT functional variant with at least 95% sequence identity to a sequence selected from the group consisting of SEQ ID NO: 5, and SEQ ID NO: 7.

30. The method of claim 1, wherein replication of the covalently closed circular plasmid occurs without production of replication intermediates.

31. The covalently closed circular plasmid of claim 18, wherein the covalently closed circular plasmid is configured to replicate without production of replication intermediates.

* * * * *

SEQUENCE LISTING

<160> NUMBER OF SEQ ID NOS: 23

<210> SEQ ID NO 1
<211> LENGTH: 281
<212> TYPE: DNA
<213> ORGANISM: Artificial Sequence
<220> FEATURE:
<223> OTHER INFORMATION: R6K gamma origin

<400> SEQUENCE: 1
ggcttgttgt ccacaaccgt taaaccttaa aagctttaaa agccttatat attctttttt    60
ttcttataaa acttaaaacc ttagaggcta tttaagttgc tgatttatat taattttatt   120
gttcaaacat gagagcttag tacgtgaaac atgagagctt agtacgttag ccatgagagc   180
ttagtacgtt agccatgagg gtttagttcg ttaaacatga gagcttagta cgttaaacat   240
gagagcttag tacgtactat caacaggttg aactgctgat c                       281

<210> SEQ ID NO 2
<211> LENGTH: 281
<212> TYPE: DNA
<213> ORGANISM: Artificial Sequence
<220> FEATURE:
<223> OTHER INFORMATION: 1 CpG R6K gamma origin

<400> SEQUENCE: 2
ggcttgttgt ccacaaccat taaaccttaa aagctttaaa agccttatat attctttttt    60
ttcttataaa acttaaaacc ttagaggcta tttaagttgc tgatttatat taattttatt   120
gttcaaacat gagagcttag tacgtgaaac atgagagctt agtacattag ccatgagagc   180
ttagtacatt agccatgagg gtttagttca ttaaacatga gagcttagta cattaaacat   240
gagagcttag tacatactat caacaggttg aactgctgat c                       281

<210> SEQ ID NO 3
<211> LENGTH: 260
<212> TYPE: DNA
<213> ORGANISM: Artificial Sequence
<220> FEATURE:
<223> OTHER INFORMATION: CpG free R6K gamma origin

<400> SEQUENCE: 3
aaaccttaaa acctttaaaa gcctatata ttcttttttt tcttataaaa cttaaaacct    60
tagaggctat ttaagttgct gatttatatt aattttattg ttcaaacatg agagcttagt   120

-continued

```
acatgaaaca tgagagctta gtacattagc catgagagct tagtacatta gccatgaggg      180
tttagttcat taaacatgag agcttagtac attaaacatg agagcttagt acatactatc      240
aacaggttga actgctgatc                                                  260

<210> SEQ ID NO 4
<211> LENGTH: 389
<212> TYPE: DNA
<213> ORGANISM: Artificial Sequence
<220> FEATURE:
<223> OTHER INFORMATION: Extended R6K gamma origin

<400> SEQUENCE: 4
tgtcagccgt taagtgttcc tgtgtcactg aaaattgctt tgagaggctc taagggcttc       60
tcagtgcgtt acatccctgg cttgttgtcc acaccgtta aaccttaaaa gctttaaaag      120
ccttatatat tctttttttt cttataaaac ttaaaacctt agaggctatt taagttgctg      180
atttatatta attttattgt tcaaacatga gagcttagta cgtgaaacat gagagcttag      240
tacgttagcc atgagagctt agtacgttag ccatgagggt ttagttcgtt aaacatgaga      300
gcttagtacg ttaaacatga gagcttagta cgtgaaacat gagagcttag tacgtactat      360
caacaggttg aactgctgat cttcagatc                                        389

<210> SEQ ID NO 5
<211> LENGTH: 139
<212> TYPE: DNA
<213> ORGANISM: Artificial Sequence
<220> FEATURE:
<223> OTHER INFORMATION: RNA-OUT selectable marker

<400> SEQUENCE: 5
gtagaattgg taaagagagt cgtgtaaaat atcgagttcg cacatcttgt tgtctgatta       60 ttgattttg gcgaaaccat ttgatcatat gacaagatgt gtatctacct taacttaatg      120
attttgataa aaatcatta                                                   139

<210> SEQ ID NO 6
<211> LENGTH: 69
<212> TYPE: DNA
<213> ORGANISM: Artificial Sequence
<220> FEATURE:
<223> OTHER INFORMATION: RNA-OUT antisense repressor RNA

<400> SEQUENCE: 6
tcgcacatct tgttgtctga ttattgattt ttggcgaaac catttgatca tatgacaaga       60
tgtgtatct                                                               69

<210> SEQ ID NO 7
<211> LENGTH: 139
<212> TYPE: DNA
<213> ORGANISM: Artificial Sequence
<220> FEATURE:
<223> OTHER INFORMATION: 2 CpG RNA-OUT selectable marker

<400> SEQUENCE: 7
gtagaattgg taaagagagt tgtgtaaaat attgagttcg cacatcttgt tgtctgatta       60 ttgattttg gcgaaaccat ttgatcatat gacaagatgt gtatctacct taacttaatg      120
attttgataa aaatcatta                                                   139

<210> SEQ ID NO 8
<211> LENGTH: 466
```

-continued

```
<212> TYPE: DNA
<213> ORGANISM: Artificial Sequence
<220> FEATURE:
<223> OTHER INFORMATION: R6K gamma origin -RNA-OUT bacterial
      replication-selection region flanked by NheI and KpnI restriction
      sites

<400> SEQUENCE: 8
gctagcccgc ctaatgagcg ggctttttttt tggcttgttg tccacaaccg ttaaacctta      60
aaagctttaa aagccttata tattctttttt tttcttataa aacttaaaac cttagaggct     120
atttaagttg ctgatttata ttaattttat tgttcaaaca tgagagctta gtacgtgaaa     180
catgagagct tagtacgtta gccatgagag cttagtacgt tagccatgag ggtttagttc     240
gttaaacatg agagcttagt acgttaaaca tgagagctta gtacgtacta tcaacaggtt     300
gaactgctga tccacgttgt ggtagaattg gtaaagagag tcgtgtaaaa tatcgagttc     360
gcacatcttg ttgtctgatt attgattttt ggcgaaacca tttgatcata tgacaagatg     420
tgtatctacc ttaacttaat gattttgata aaaatcatta ggtacc                    466

<210> SEQ ID NO 9
<211> LENGTH: 439
<212> TYPE: DNA
<213> ORGANISM: Artificial Sequence
<220> FEATURE:
<223> OTHER INFORMATION: 1 CpG R6K gamma origin - 2 CpG RNA-OUT
      bacterial replication-selection region flanked by NheI and KpnI
      restriction sites

<400> SEQUENCE: 9
gctagctggc ttgttgtcca caaccattaa accttaaaag ctttaaaagc cttatatatt      60
cttttttttc ttataaaact taaaacctta gaggctattt aagttgctga tttatattaa     120
ttttattgtt caaacatgag agcttagtac gtgaaacatg agagcttagt acattagcca     180
tgagagctta gtacattagc catgaggggtt tagttcatta aacatgagag cttagtacat     240
taaacatgag agcttagtac atactatcaa caggttgaac tgctgatctg tacagtagaa     300
ttggtaaaga gagttgtgta aaatattgag ttcgcacatc ttgttgtctg attattgatt     360
tttggcgaaa ccatttgatc atatgacaag atgtgtatct accttaactt aatgattttg     420
ataaaaatca ttaggtacc                                                  439

<210> SEQ ID NO 10
<211> LENGTH: 565
<212> TYPE: DNA
<213> ORGANISM: Artificial Sequence
<220> FEATURE:
<223> OTHER INFORMATION: pNTC-NP1 polylinker trpA R6K-RNA-OUT polylinker
      cloning cassette: EcoRI-HindIII

<400> SEQUENCE: 10
gaattcgagc tcggtacctc gcgaatgcat ctaggggacg gccgctagcc cgcctaatga      60
gcgggctttt ttttggcttg ttgtccacaa ccgttaaacc ttaaaagctt taaaagcctt     120
atatattctt tttttcttaa taaaacttaa aaccttagag gctatttaag ttgctgattt     180
atattaattt tattgttcaa acatgagagc ttagtacgtg aaacatgaga gcttagtacg     240
ttagccatga gagcttagta cgttagccat gaggggtttag ttcgttaaac atgagagctt     300
agtacgttaa acatgagagc ttagtacgta ctatcaacag gttgaactgc tgatccacgt     360
tgtggtagaa ttggtaaaga gagtcgtgta aaatatcgag ttcgcacatc ttgttgtctg     420
attattgatt tttggcgaaa ccatttgatc atatgacaag atgtgtatct accttaactt     480
```

```
aatgattttg ataaaaatca ttaggagcta gcattgggtc atcggatccc gggcccgtcg      540
actgcagagg cctgcatgca agctt                                            565
```

```
<210> SEQ ID NO 11
<211> LENGTH: 584
<212> TYPE: DNA
<213> ORGANISM: Artificial Sequence
<220> FEATURE:
<223> OTHER INFORMATION: pNTC-NP2 polylinker trpA R6K-RNA-OUT polylinker
      cloning cassette: EcoRI-HindIII

<400> SEQUENCE: 11
```

```
gaattcgagc tcggtacctc gcgaatgcat ctaggggacg gccgctagcc cgcctaatga       60
gcgggctttt ttttggcttg ttgtccacaa ccgttaaacc ttaaaagctt taaaagcctt      120
atatattctt ttttttctta taaaacttaa aaccttagag gctatttaag ttgctgattt      180
atattaattt tattgttcaa acatgagagc ttagtacgtg aaacatgaga gcttagtacg      240
ttagccatga gagcttagta cgttagccat gagggtttag ttcgttaaac atgagagctt      300
agtacgttaa acatgagagc ttagtacgta ctatcaacag gttgaactgc tgatccacgt      360
tgtggtagaa ttggtaaaga gagtcgtgta aaatatcgag ttcgcacatc ttgttgtctg      420
attattgatt tttggcgaaa ccatttgatc atatgacaag atgtgtatct accttaactt      480
aatgattttg ataaaaatca ttaggactag tcccgggcgc tagttattaa tattgggtca      540
tcggatcccg ggcccgtcga ctgcagaggc ctgcatgcaa gctt                       584
```

```
<210> SEQ ID NO 12
<211> LENGTH: 557
<212> TYPE: DNA
<213> ORGANISM: Artificial Sequence
<220> FEATURE:
<223> OTHER INFORMATION: pNTC-NP3 polylinker trpA R6K-RNA-OUT polylinker
      cloning cassette: EcoRI-HindIII

<400> SEQUENCE: 12
```

```
gaattcgagc tcggtacctc gcgaatgcat ctaggggacg gccgctagcc cgcctaatga       60
gcgggctttt ttttggcttg ttgtccacaa ccgttaaacc ttaaaagctt taaaagcctt      120
atatattctt ttttttctta taaaacttaa aaccttagag gctatttaag ttgctgattt      180
atattaattt tattgttcaa acatgagagc ttagtacgtg aaacatgaga gcttagtacg      240
ttagccatga gagcttagta cgttagccat gagggtttag ttcgttaaac atgagagctt      300
agtacgttaa acatgagagc ttagtacgta ctatcaacag gttgaactgc tgatccacgt      360
tgtggtagaa ttggtaaaga gagtcgtgta aaatatcgag ttcgcacatc ttgttgtctg      420
attattgatt tttggcgaaa ccatttgatc atatgacaag atgtgtatct accttaactt      480
aatgattttg ataaaaatca ttaggtaccg agctcggatc ccgggcccgt cgactgcaga      540
ggcctgcatg caagctt                                                     557
```

```
<210> SEQ ID NO 13
<211> LENGTH: 557
<212> TYPE: DNA
<213> ORGANISM: Artificial Sequence
<220> FEATURE:
<223> OTHER INFORMATION: pNTC-NP4 polylinker trpA R6K-RNA-OUT polylinker
      cloning cassette: HindIII-EcoRI

<400> SEQUENCE: 13
```

```
aagcttgcat gcaggcctct gcagtcgacg ggcccgggat ccgagctcgg tacctcgcga       60
```

```
atgcatctag gggacggccg ctagcccgcc taatgagcgg gctttttttt ggcttgttgt      120
ccacaaccgt taaaccttaa aagctttaaa agccttatat attctttttt ttcttataaa      180
acttaaaacc ttagaggcta tttaagttgc tgatttatat taattttatt gttcaaacat      240
gagagcttag tacgtgaaac atgagagctt agtacgttag ccatgagagc ttagtacgtt      300
agccatgagg gtttagttcg ttaaacatga gagcttagta cgttaaacat gagagcttag      360
tacgtactat caacaggttg aactgctgat ccacgttgtg gtagaattgg taaagagagt      420
cgtgtaaaat atcgagttcg cacatcttgt tgtctgatta ttgatttttg gcgaaaccat      480
ttgatcatat gacaagatgt gtatctacct taacttaatg attttgataa aaatcattag      540
gtaccgagct cgaattc                                                      557
```

<210> SEQ ID NO 14
<211> LENGTH: 503
<212> TYPE: DNA
<213> ORGANISM: Artificial Sequence
<220> FEATURE:
<223> OTHER INFORMATION: pNTC-NP5 polylinker trpA R6K-RNA-OUT polylinker
      cloning cassette: KasI-HindIII

<400> SEQUENCE: 14

```
ggcgccgcta gcccgcctaa tgagcgggct ttttttggc ttgttgtcca caaccgttaa        60
accttaaaag ctttaaaagc cttatatatt cttttttttc ttataaaact taaaaccttaa      120 gaggctattt aagttgctga tttatattaa ttttattgtt caaacatgag agcttagtac      180
gtgaaacatg agagcttagt acgttagcca tgagagctta gtacgttagc catgaggggtt      240 tagttcgtta aacatgagag cttagtacgt taaacatgag agcttagtac gtactatcaa      300
caggttgaac tgctgatcca cgttgtggta gaattggtaa agagagtcgt gtaaaatatc      360
gagttcgcac atcttgttgt ctgattattg attttttggcg aaaccatttg atcatatgac      420
aagatgtgta tctaccttaa cttaatgatt ttgataaaaa tcattaggta ccacatgtcc      480
tgcagaggcc tgcatgcaag ctt                                               503
```

<210> SEQ ID NO 15
<211> LENGTH: 539
<212> TYPE: DNA
<213> ORGANISM: Artificial Sequence
<220> FEATURE:
<223> OTHER INFORMATION: pNTC-NP6 polylinker trpA R6K-RNA-OUT polylinker
      cloning cassette: EcoRI-SacI

<400> SEQUENCE: 15

```
gaattctgca gatatccatc acactggcgg ccgctagccc gcctaatgag cgggcttttt       60
tttggcttgt tgtccacaac cgttaaacct taaaagcttt aaaagcctta tatattcttt      120
tttttcttat aaaacttaaa accttagagg ctatttaagt tgctgattta tattaatttt      180
attgttcaaa catgagagct tagtacgtga aacatgagag cttagtacgt tagccatgag      240
agcttagtac gttagccatg agggtttagt tcgttaaaca tgagagctta gtacgttaaa      300
catgagagct tagtacgtac tatcaacagg ttgaactgct gatccacgtt gtggtagaat      360
tggtaaagag agtcgtgtaa aatatcgagt tcgcacatct tgttgtctga ttattgattt      420
ttggcgaaac catttgatca tatgacaaga tgtgtatcta ccttaactta atgattttga      480
taaaaatcat taggtaccgg gcccccctc gatcgaggtc gacggtatcg ggggagctc         539
```

<210> SEQ ID NO 16

```
<211> LENGTH: 500
<212> TYPE: DNA
<213> ORGANISM: Artificial Sequence
<220> FEATURE:
<223> OTHER INFORMATION: pNTC-NP7 polylinker trpA R6K-RNA-OUT polylinker
      cloning cassette: BssHII-BssHII

<400> SEQUENCE: 16
gcgcgcagcc ttaattaagc tagcccgcct aatgagcggg cttttttttg gcttgttgtc      60
cacaaccgtt aaaccttaaa agctttaaaa gccttatata ttcttttttt tcttataaaa     120
cttaaaacct tagaggctat ttaagttgct gatttatatt aattttattg ttcaaacatg     180
agagcttagt acgtgaaaca tgagagctta gtacgttagc catgagagct tagtacgtta     240
gccatgaggg tttagttcgt taaacatgag agcttagtac gttaaacatg agagcttagt     300
acgtactatc aacaggttga actgctgatc cacgttgtgg tagaattggt aaagagagtc     360
gtgtaaaata tcgagttcgc acatcttgtt gtctgattat tgatttttgg cgaaaccatt     420
tgatcatatg acaagatgtg tatctacctt aacttaatga ttttgataaa aatcattagg     480
taccttaatt aactgcgcgc                                                500

<210> SEQ ID NO 17
<211> LENGTH: 530
<212> TYPE: DNA
<213> ORGANISM: Artificial Sequence
<220> FEATURE:
<223> OTHER INFORMATION: pNTC-3xCpG NP1 polylinker R6K-RNA-OUT
      polylinker cloning cassette: HindIII-EcoRI

<400> SEQUENCE: 17
aagcttgcat gcaggcctct gcagtcgacg ggccctctag actcgagctg gcttgttgtc      60
cacaaccatt aaaccttaaa agctttaaaa gccttatata ttcttttttt tcttataaaa     120
cttaaaacct tagaggctat ttaagttgct gatttatatt aattttattg ttcaaacatg     180
agagcttagt acgtgaaaca tgagagctta gtacattagc catgagagct tagtacatta     240
gccatgaggg tttagttcat taaacatgag agcttagtac attaaacatg agagcttagt     300
acatactatc aacaggttga actgctgatc tgtacagtag aattggtaaa gagagttgtg     360
taaaatattg agttcgcaca tcttgttgtc tgattattga ttttttggcga aaccatttga     420 tcatatgaca agatgtgtat ctaccttaac ttaatgattt tgataaaaat cattaggtac     480
cgctagcggc cgtcccctag atgcattcgc gaggtaccga gctcgaattc             530

<210> SEQ ID NO 18
<211> LENGTH: 303
<212> TYPE: DNA
<213> ORGANISM: Artificial Sequence
<220> FEATURE:
<223> OTHER INFORMATION: R6K gamma origin -7 iteron

<400> SEQUENCE: 18
ggcttgttgt ccacaaccgt taaaccttaa aagctttaaa agccttatat attctttttt      60
ttcttataaa acttaaaacc ttagaggcta tttaagttgc tgatttatat taattttatt     120
gttcaaacat gagagcttag tacgtgaaac atgagagctt agtacgttag ccatgagagc     180
ttagtacgtt agccatgagg gtttagttcg ttaaacatga gagcttagta cgttaaacat     240
gagagcttag tacgttaaac atgagagctt agtacgtact atcaacaggt tgaactgctg     300
atc                                                                 303
```

US 12,600,984 B2

57 58

-continued

```
<210> SEQ ID NO 19
<211> LENGTH: 22
<212> TYPE: DNA
<213> ORGANISM: Artificial Sequence
<220> FEATURE:
<223> OTHER INFORMATION: R6K gamma origin iteron

<400> SEQUENCE: 19
aaacatgaga gcttagtacg tg                                          22

<210> SEQ ID NO 20
<211> LENGTH: 22
<212> TYPE: DNA
<213> ORGANISM: Artificial Sequence
<220> FEATURE:
<223> OTHER INFORMATION: R6K gamma origin iteron

<400> SEQUENCE: 20
aaacatgaga gcttagtacg tt                                          22

<210> SEQ ID NO 21
<211> LENGTH: 22
<212> TYPE: DNA
<213> ORGANISM: Artificial Sequence
<220> FEATURE:
<223> OTHER INFORMATION: R6K gamma origin iteron

<400> SEQUENCE: 21
agccatgaga gcttagtacg tt                                          22

<210> SEQ ID NO 22
<211> LENGTH: 22
<212> TYPE: DNA
<213> ORGANISM: Artificial Sequence
<220> FEATURE:
<223> OTHER INFORMATION: R6K gamma origin iteron

<400> SEQUENCE: 22
agccatgagg gtttagttcg tt                                          22

<210> SEQ ID NO 23
<211> LENGTH: 22
<212> TYPE: DNA
<213> ORGANISM: Artificial Sequence
<220> FEATURE:
<223> OTHER INFORMATION: R6K gamma origin iteron

<400> SEQUENCE: 23
aaacatgaga gcttagtacg ta                                          22
```